United States Patent [19]

Nonami et al.

[11] Patent Number: 5,795,151
[45] Date of Patent: Aug. 18, 1998

[54] GLASS MATERIAL, LIVING TISSUE REPLACEMENT, AND ORTHODONTIC PART

[75] Inventors: Toru Nonami; Chihiro Takahashi; Tatsuji Sano, all of Chiba, Japan

[73] Assignee: TDK Corporation, Tokyo, Japan

[21] Appl. No.: 669,319

[22] PCT Filed: Nov. 28, 1995

[86] PCT No.: PCT/JP95/02419

§ 371 Date: Jul. 9, 1996

§ 102(e) Date: Jul. 9, 1996

[87] PCT Pub. No.: WO96/16683

PCT Pub. Date: Jun. 6, 1996

[30] Foreign Application Priority Data

Nov. 30, 1994 [JP] Japan ............... 6-321358
Aug. 4, 1995 [JP] Japan ............... 7-219849

[51] Int. Cl.$^6$ .............. A61C 3/00; A61C 8/00
[52] U.S. Cl. .............. 433/8; 433/173; 501/100
[58] Field of Search .............. 433/8, 9, 10, 11, 433/12, 13, 14, 15, 16, 17, 201.1; 501/11, 27, 41, 100, 101, 102, 103, 104, 105

[56] References Cited

U.S. PATENT DOCUMENTS 5,145,365 9/1992 Farzin-Nia et al. .......... 433/8
5,231,062 7/1993 Mathers et al. .......... 433/8 X
5,261,814 11/1993 Farzin-Nia et al. .......... 433/8

FOREIGN PATENT DOCUMENTS 56-7708 1/1981 Japan.
2231668 10/1987 Japan.
63-82670 4/1988 Japan.

*Primary Examiner*—Nicholas D. Lucchesi
*Attorney, Agent, or Firm*—Oblon, Spivak, McClelland, Maier & Neustadt, P.C.

[57] ABSTRACT

A glass material of the invention contains $SiO_2$, MgO, $Al_2O_3$, and $TiO_2$ as main components in amounts of 40–65% by weight of $SiO_2$, 9–30% by weight of MgO, 8–31% by weight of $Al_2O_3$, and 6–15% by weight of $TiO_2$, and satisfies expression I: $\{100-(A+S+T)\}/S \geq 0.340$ wherein A, S and T are contents in % by weight of $Al_2O_3$, $SiO_2$, and $TiO_2$, respectively, and Expression II: $(S+M)/4 > 100-(S+M+A+T)$ wherein M is a content in % by weight of MgO, and is substantially free of fluorine. It is used in the preparation of a living tissue replacement or orthodontic part. A living tissue replacement and orthodontic part which experience a minimal loss of material properties in a deleterious environment as in the oral cavity and should have a complex shape as in the case of a dental crown repair, high strength and aesthetic appearance can be briefly prepared in a safe manner without using a special manufacturing apparatus.

13 Claims, 13 Drawing Sheets

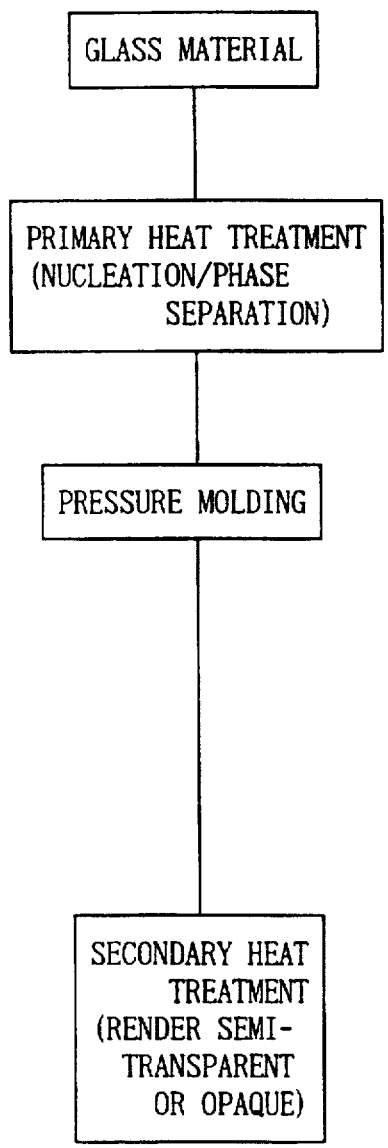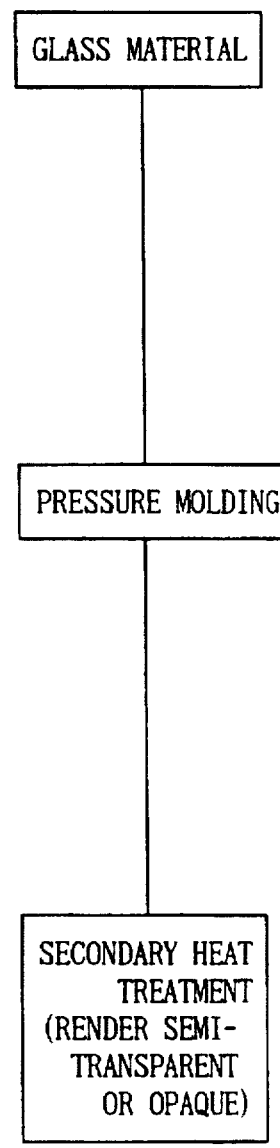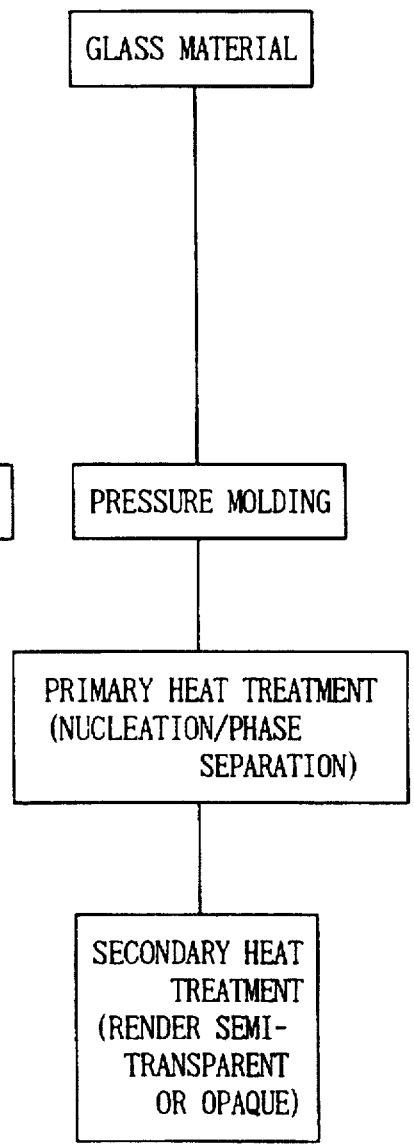

FIG. 12
(a)
FIG. 12
(b)
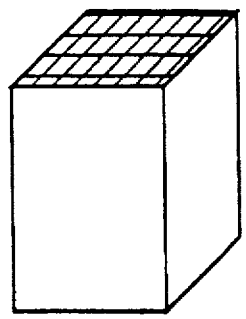
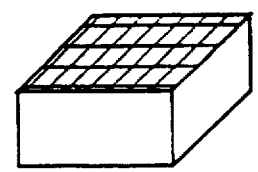
FIG. 12
(c)
FIG. 12
(d)
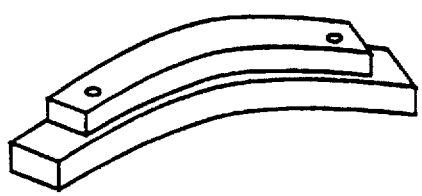
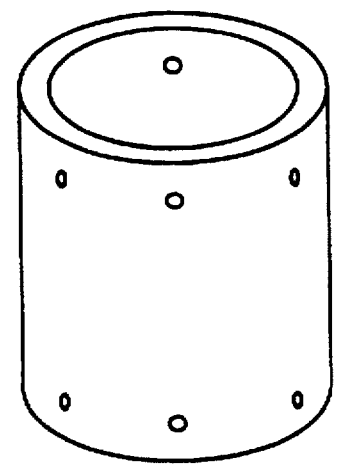
FIG. 12
(e)
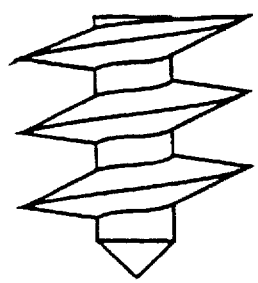

FIG.13 (a)
FIG.13 (b)
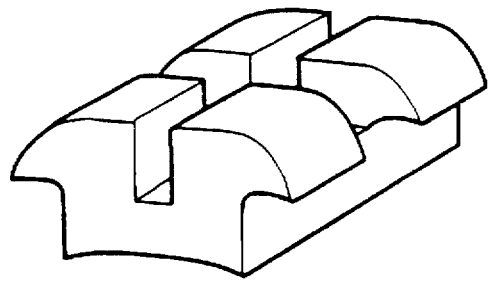
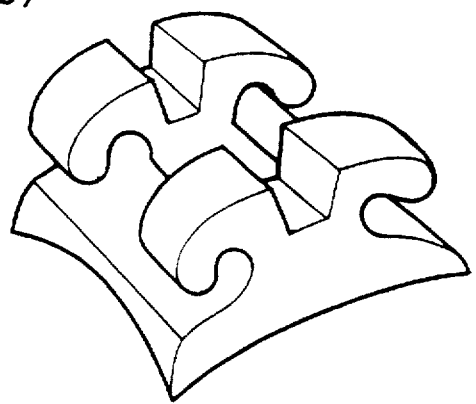
FIG.13 (c)
FIG.13 (d)
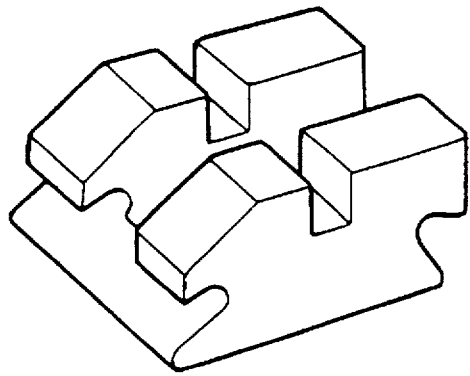
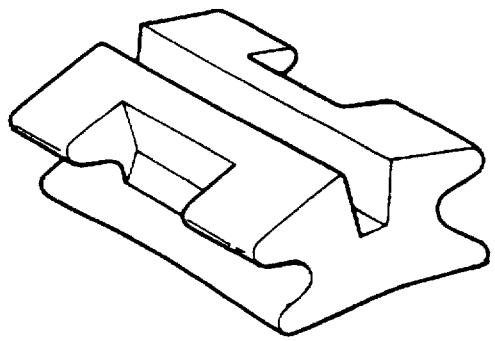

GLASS MATERIAL, LIVING TISSUE REPLACEMENT, AND ORTHODONTIC PART

TECHNICAL FIELD

This invention relates to living tissue replacements made of semi-transparent or opaque glass and applicable as artificial dental crowns, artificial dental roots, artificial bones, bone screws, and artificial tracheas, orthodontic parts made of glass, and glass materials from which these parts are formed.

BACKGROUND ART

Alumina ceramics and various metal materials are used to form living tissue replacements such as artificial dental crowns, artificial dental roots, artificial bones, artificial junctions and bone fillers. However, metal materials suffer from a problem that metal ions are dissolved out. When metal materials are used as artificial dental crowns, their aesthetic appearance is poor. On the other hand, alumina ceramics are free from the concern about hazard to human bodies, but difficult to work into complex shapes. A great attention is paid to crystallized glass as dental repairs because of good biological affinity and high mechanical strength, and various proposals have been made therefor. In most of crystallized glass materials proposed as dental material, crystals of mica systems or calcium phosphate systems including apatite are precipitated. Therefore, alkali metal elements or phosphorus is an essential component and they are contained in relatively large amounts. However, alkali metal elements deteriorate the water resistance of glass while phosphorus-containing crystals and glass of calcium phosphate systems including apatite deteriorate acid resistance. Although crystallization improves chemical durability, a vitreous phase coexists with a crystalline phase in the case of crystallized glass, especially dental crown repairs where aesthetic appearance is keenly desired. It is thus understood that the relatively high content of alkali metal elements and phosphorus potentially involves a crucial problem to glass for use in the oral cavity which presents a rigorous environment to glass.

Glass materials which do not contain alkali metal elements and phosphorus as essential elements are described, for example, in Japanese Patent Publication (JP-B) No. 36107/1992 and "Fine Ceramics," Vol. 3, pp. 79–87, 1982.

JP-B 36107/1992 discloses crystallized glass for use as artificial bones and dental materials. This crystallized glass has a non-calcium phosphate system composition free of $P_2O_5$. More particularly, it is "a $P_2O_5$-free crystallized glass having a composition wherein at least 90% consists of, in % by weight, $SiO_2$ 48.2 to 53.0%,
CaO 35.9 to 44.0%, and
MgO 3.5 to 7.5%, and up to 10% consists of impurities, the crystallized glass possessing a structure having numerous fine wollastonite ($CaO.SiO_2$) grains and diopside ($CaO.MgO.2SiO_2$) grains dispersed in glass."

The crystallized glass disclosed in "Fine Ceramics," Vol. 3 has a composition comprising, in % by weight, $SiO_2$ 43 to 52%,
$Al_2O_3$ 25 to 31%,
MgO 11 to 14%,
$TiO_2$ 8 to 12%, and
$CaF_2$ 0 to 2%."

The crystallized glass described in JP-B 36107/1992 is prepared by molding glass powder, followed by firing and crystallization treatment. With the process of molding and firing glass powder, it is difficult to prepare dental crowns and other parts of complex shape. Since the molding step uses an isostatic press and the firing step uses a high temperature of 1,050° C. as described in the publication, this process is quite difficult to practice in the dental office. The process takes a long time to completion since the firing step uses a slow heating rate of 30° to 60° C./hour and a slow cooling rate of 30° to 120° C./hour. Dimensional precision is low since firing entails a large shrinkage factor. Firing of powder after molding fails to provide sufficient strength. Preparation of glass powder requires cumbersome operation and considerable costs because molten glass must be converted into ribbon shape as by passing through water-cooled rollers. With this procedure, many voids are left after firing. Since biotic replacements vary in dimensions depending on a particular individual or application, it is important that doctors, dentists, and dental technicians can purchase the material at low cost and work it in a safe and simple manner using the existing machine. Conventional furnaces use different heaters and housing materials depending on the service temperature range and are generally classified into furnaces for use at temperatures of lower than 1,000° C., 1,000° to 1,300° C., 1,300° to 1,600° C., and higher than 1,600° C. The furnaces which can be used at higher temperatures are more expensive. With these factors taken into account, it is desirable that glass material be molded and crystallized at temperatures below 1,000° C. Glass materials of the composition described in "Fine Ceramics," Vol. 3, however, cannot be pressure molded in a substantial sense because when a glass ingot is heated from its glass transition temperature, crystallization occurs before its viscosity becomes fully low. Therefore, for molding, the glass material must be cast from a molten state at 1,500° C. or higher. Then the dental technician who practically works the material into a living tissue replacement must furnish an expensive manufacturing equipment and the operation is dangerous because of the high temperature. The glass aterial may contain $CaF_2$ although fluorine is so volatile upon melting as to hinder the reproduction of such a composition, promotes crystallization to restrict molding, and can deteriorate the furnace. In addition, volatile fluorine is undesirably hazardous to the human body.

Like artificial dental crowns, orthodontic parts are also used in the oral cavity. Orthodontic parts are appliances for correcting dental malalignment. Typically, a bracket configured as shown in FIG. 13 is mounted to teeth by fastening with an arch wire. Since orthodontic parts are also used for a long time in the oral cavity, they are required to be chemically durable, safe to the human body, and aesthetic as are the artificial dental crowns. In the prior art, metals such as stainless steel and resins such as polycarbonate are used as the material of which orthodontic parts are made while the use of polycrystalline and single crystal ceramics has also been proposed. Metallic materials are strong and well workable, but leave an aesthetic problem since they have metallic luster and are conspicuous. Resinous materials are acceptable in aesthetic appearance since they are transparent and inconspicuous, but have low strength with respect to metallic arch wires and are less slippery to metallic arch wires, and less durable, achieving insufficient orthodontic effect. The resinous materials also have a problem of easy discoloring. Japanese Patent Application Kokai (JP-A) No. 89153/1988 proposes the use of polycrystalline ceramics.

The orthodontic part disclosed in this publication is formed of a sintered body represented by the general formula MgO.(1±χ)Al₂O₃ wherein χ≦0.1 and having a mean grain size of up to 100 μm, light transparency, and a spinel structure. However, since the polycrystalline ceramics are sintered after molding, maintenance of a dimensional precision is difficult due to shrinkage upon sintering, and machining after sintering is also difficult. In Example of the above-referred publication, sintering for 10 hours at 1,750° C. is followed by sintering for 2 hours at 1,400° C. under a pressure force of 2 tons in a hot isostatic press (HIP) in order to improve light transparency and mechanical strength. This manufacture needs a high temperature, high pressure and long time. JP-A 46451/1989 proposes the use of single crystal ceramics. The orthodontic bracket described in this publication is formed of single crystal zirconia which contains yttria in order to ensure transparency and strength. The single crystal, however, is expensive, cumbersome to prepare, and inadequate for mass scale production.

DISCLOSURE OF THE INVENTION

An object of the invention is to make it possible to prepare a living tissue replacement which undergoes minimal deterioration of material properties under a rigorous environment as in the oral cavity and has high strength, especially a living tissue replacement which has a complex shape and must have aesthetic appearance like dental crown repairs and an orthodontic part briefly in a safe manner without using a special manufacturing equipment.

This and other objects are achieved by the present invention which is defined below as (1) to (13).

(1) A glass material for use in the preparation of living tissue replacements and orthodontic parts, comprising silicon oxide, magnesium oxide, aluminum oxide, and titanium oxide as main components, the content of these components, when calculated as $SiO_2$, $MgO$, $Al_2O_3$, and $TiO_2$, respectively, and expressed by percent by weight, being $SiO_2$ 40 to 65% by weight, $MgO$ 9 to 30% by weight, $Al_2O_3$ 8 to 31% by weight, and $TiO_2$ 6 to 15% by weight, the material satisfying expression I:

$$\{100-(A+S+T)\}/S \geq 0.340 \quad \text{I:}$$

wherein A, S and T are contents in % by weight of $Al_2O_3$, $SiO_2$, and $TiO_2$, respectively, and Expression II:

$$(S+M)/4 > 100-(S+M+A+T) \quad \text{II:}$$

wherein M is a content in % by weight of MgO, and being substantially free of fluorine.

(2) The glass material of (1) further comprising at least one of Ca, Ba, and Zn as an auxiliary component, wherein the sum of CaO+BaO+ZnO is up to 20% by weight when Ca, Ba, and Zn are calculated as CaO, BaO, and ZnO, respectively.

(3) The glass material of (1) or (2) further comprising at least one of Pd, Pt, Ag, Au, Re, Ru, Rh, and Ir as an auxiliary component in a total content of up to 1% by weight.

(4) The glass material of any one of (1) to (3) further comprising at least one of Mn, Fe, Ni, and Ce as an auxiliary component, wherein the sum of Mno+FeO+NiO+CeO₂ is up to 2% by weight when Mn, Fe, Ni, and Ce are calculated as MnO, FeO, NiO, and CeO₂, respectively.

(5) The glass material of any one of (1) to (4) further comprising at least one of Li, Na, K, and P as an auxiliary component, wherein the sum of $Li_2O+Na_2O+K_2O+P_2O_5$ is up to 5% by weight when Li, Na, K, and P are calculated as $Li_2O$, $Na_2O$, $K_2O$, and $P_2O_5$, respectively.

(6) The glass material of any one of (1) to (5) further comprising Zr as an auxiliary component, wherein the content of $ZrO_2$ is up to 5% by weight when Zr is calculated as $ZrO_2$.

(7) The glass material of any one of (1) to (6) further comprising B as an auxiliary component, wherein the content of $B_2O_3$ is up to 5% by weight when B is calculated as $B_2O_3$.

(8) The glass material of any one of (1) to (7) further comprising nitrogen, wherein the content of $Si_3N_4$ is up to 4% by weight when nitrogen is calculated as $Si_3N_4$.

(9) The glass material of any one of (1) to (8) wherein when compressed under an initial pressure of 1.8 MPa and then heated from its glass transition temperature to 1,000° C. at a rate of 5° C./min. while being compressed under a constant load, the material is deformable at least 85% in the pressure applied direction.

(10) The glass material of any one of (1) to (9) wherein the material has a viscosity η (P) and the material can maintain for at least 7 minutes the state that logη is up to 7.6 at a heating rate of 5° C./min. in the heating step from the glass transition temperature to 1,000° C.

(11) The glass material of any one of (1) to (10) wherein the material has a viscosity η (P) and the minimum of logη is up to 7.0 in the heating step from the glass transition temperature to 1,000° C.

(12) A living tissue replacement prepared by shaping a glass material according to any one of (1) to (11) and treating it to be substantially semi-transparent or opaque.

(13) An orthodontic part prepared by shaping a glass material according to any one of (1) to (11).

The glass material of the invention can be pressure molded by utilizing the viscous flow phenomenon which occurs at temperatures in the range from the glass transition temperature to less than the liquidus temperature when the material is heated from a lower temperature side. Utilization of the viscous flow of glass permits the glass material to be easily molded into a desired shape such as a dental crown within a short time without using a special manufacturing equipment. In addition, the temperature required for molding is as low as 1,000° C. or lower and the pressure applied is as low as about 5 MPa or lower.

Also, the living tissue replacement obtained by processing the glass material to be substantially semi-transparent or opaque through crystallization or the like has aesthetic appearance and fully satisfactory acid and water resistance. When applied as dental crowns or the like, dissolution and performance loss such as strength loss little occur even in a rigorous environment as in the oral cavity. Since prior art crystallized glass for dental crowns has less environment resistance and insufficient aesthetic appearance as dental crowns, it must be subject to porcelain baking or staining on the surface when it is applied as dental crowns. Such a dental crown can be deteriorated because the glass base is exposed when the dental crown is secured to the diseased site and fine dimensional errors are drilled off. In contrast, the living tissue replacement of the invention little deteriorates in the oral cavity and is substantially free from the risk of deterioration even when the glass base is exposed by dimensional error correction or other causes.

Moreover, the living tissue replacement of the invention possesses at least equal mechanical strength to prior art biotic crystallized glass essentially requiring the addition of alkali metal elements and phosphorus. The prior art crystallized glass has noble metals added for the purposes of improving aesthetic appearance, improving strength and reducing the working time upon crystallization although the addition of noble metals results in difficultly reproducible benefits and adds to the cost. In contrast, the living tissue replacement of the invention has superior aesthetic appearance and strength without addition of noble metals and can be briefly treated to be semi-transparent or opaque through crystallization or the like.

Like the living tissue replacement mentioned above, the orthodontic part of the invention can be prepared by pressure molding utilizing the viscous flow phenomenon. Even a complex shape can be easily prepared. Since the part as superior environment resistance in the oral cavity, good slippage to metallic arch wires, and high mechanical strength, it is effective for correcting dental malalignment. Because of full transparency available, the part is acceptable from the aesthetic standpoint.

More particularly, the following benefits are achieved by the invention.

(1) Glass material can be molded by compressing at a temperature lower than the liquidus temperature, preferably lower than the crystallization temperature, for example, up to 1,000° C., especially up to 900° C. Thus an inexpensive furnace may be used. Heating is possible with a conventional furnace that a dentist or dental technician uses. There is no need for atmosphere control because denaturing of glass material by oxidation does not occur even when molding is done in air. Soft investment compound can be used as the mold for molding and the glass material is mold releasable so that removal from the mold is easy.

(2) Molding is possible under a pressure of 5 MPa or lower, especially 0.3 MPa or lower. No special compression equipment is needed and molding can be done using a hand press or weight, for example. A high strength mold is unnecessary. Therefore, molding can be easily done in ordinary dental offices.

(3) As opposed to the method of molding and firing powder, neither a special mold nor equipment (e.g., CIP) is necessary and a conventional dental molding mold is usable.

(4) The method of molding and firing powder is difficult to produce parts with good dimensional precision because of an increased shrinkage factor upon sintering due to the presence of pores in the parts. In contrast, the present invention eliminates generation of pores because bulk glass material is molded under pressure. It is generally believed that to establish a semi-transparent state is very important for dental crowns from the aesthetic standpoint. For crystallized glass, it is necessary to uniformly precipitate fine crystal grains in the glass interior in order to establish a semi-transparent state. However, since the crystalline phase generally has a greater density than the vitreous phase, voids can be formed in the glass interior as a result of treatment for semi-transparency, adversely affecting strength. In contrast, the glass material of the invention can be minimized in density increase resulting from the treatment for semi-transparency or opaqueness.

(5) The method of molding powder is difficult to produce dental crowns and orthodontic parts having a complex shape. Since the present invention carries out molding by softening and fluidizing bulk glass material, a complex shape can be easily obtained like centrifugal casting. The molded part has sufficient homogeneity after it is treated to be semi-transparent or opaque by crystallization or the like. In addition, since few bubble entrapment is observed as opposed to the centrifugal casting, higher strength is obtained and the occurrence of defective parts is drastically reduced.

(6) Since glass material is not melted upon molding as opposed to the centrifugal casting, the glass material may be subject to heat treatment for nucleation or phase separation prior to pressure molding as shown in FIG. 1(a). More specifically, when the invention is applied to the preparation of a dental crown, for example, the glass material may have been heat treated for nucleation or phase separation prior to delivery to the dentist or dental technician. Then it is only required in the dental office to carry out molding to dental crown finishing steps, leading to a substantial reduction of the working time in the dental office. Also, since the time required for the glass material of the invention to turn semi-transparent or opaque through crystallization or the like is short, as shown in FIGS. 1(b) and 1(c), a living tissue replacement can be obtained within a short time after pressure molding even when heat treatment for nucleation or phase separation prior to pressure molding is omitted.

(7) Since a living tissue replacement is prepared according to the invention by molding a homogeneous bulk glass material without melting, and then treating it to be semi-transparent or opaque, fully high strength is accomplished. If the glass material is partially melted during molding, the structure after crystallization would not be homogeneous, failing to provide sufficient strength. The present invention eliminates this risk.

By the way, JP-A 231655/1987 describes a method for preparing a dental appliance by molding a ceramic material or alloy which can be plasticized by heating, but does not refer to crystallized glass. When a dental crown is prepared in one Example of this patent reference, a mixture of a glass-forming base, aluminum oxide for imparting necessary strength, a flux such as $K_2O$, $Na_2CO_3$, CaO and $B_2O_3$, and a plasticizer such as glycerin is molded. It is understood that aluminum oxide is used to impart strength since the glass is not crystallized in this Example. This product has insufficient strength as compared with the living tissue replacement prepared according to the invention. Since homogeneous crystallization is inhibited due to the containment of flux, it would be difficult to achieve satisfactory strength even if the product is crystallized.

JP-A 32867/1989 discloses "a biotic material having short fibers or whiskers uniformly dispersed in a glass ceramic sintered body, said glass ceramic consisting essentially of, in % by weight based on oxides, $SiO_2$: 40 to 70

$Al_2O_3$: 15 to 40

MgO: 15 to 30

$SiO_2+Al_2O_3+MgO$: 70 to 100

CaO+SrO+BaO: 0 to 5

$Na_2O+K_2O+Li_2O$: 0 to 7

$TiO_2+ZrO_2$: 0 to 10

$P_2O_5$: 0 to 10."

The glass ceramic in this biotic material has a crystalline phase containing at least one of cordierite, enstatite, and forsterite. As the short fibers or whiskers, there is used at least one of metal oxides, carbides, borides, and nitrides and carbon, for example, SiC, $Si_3N_4$, and $Al_2O_3$, in a total volume of 10 to 60%. Although the compositional range of the glass ceramic described in this patent reference overlaps the compositional range of the glass material of the present invention, the patent reference does not describe that the content of $Al_2O_3$, $SiO_2$, and $TiO_2$ should be controlled to satisfy expression I: $\{100-(A+S+T)\}/S \geq 0.340$. The patent reference describes no examples of glass ceramics whose composition falls in the compositional range of the glass material of the present invention. Since the biotic material described in the patent reference is prepared by molding and sintering glass powder like the crystallized glass described in the above-referred JP-B 36107/1992, it tends to contain pores, requires a high pressure force in order to achieve sufficient strength, and is difficult to mold to a complex shape and to reduce the cost. Since short fibers or whiskers are mixed with glass powder, the operation is cumbersome and a special apparatus and skill are necessary to achieve uniform mixing. The biotic material obtained by mixing short fibers or whiskers followed by sintering does not show fluidity similar to the glass material of the present invention.

BRIEF DESCRIPTION OF THE DRAWINGS

FIGS. 1(a), 1(b) and 1(c) are flow charts illustrating a process of preparing a living tissue replacement according to the invention.

FIG. 12 illustrates examples of the living tissue replacement to which the invention is applicable, FIGS. 12(a), 12(b), 12(c) and 12(d) being perspective views of an artificial corpus vertebrae, artificial intervertebral disk, artificial ilium and artificial trachea, respectively, and FIG. 12(e) being a side view of a bone screw.

FIGS. 13(a), 13(b), 13(c) and 13(d) are perspective views of exemplary orthodontic parts according to the invention.

BEST MODE FOR CARRYING OUT THE INVENTION

Figure 2:
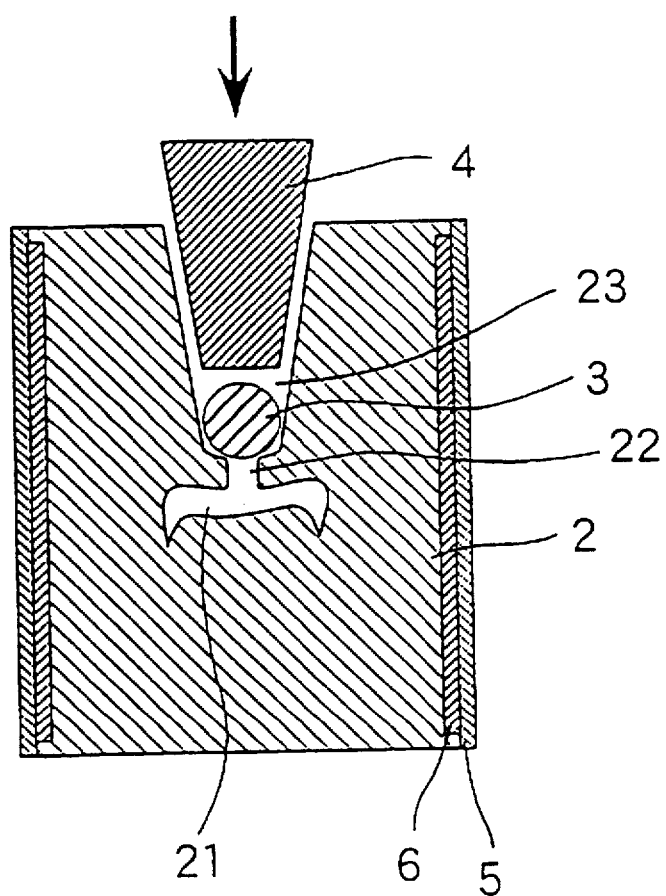
FIG. 2 illustrates one example of a pressure molding step.

Now the construction of the invention is described in detail.

The glass material of the invention is formed into a living tissue replacement such as a dental crown or an orthodontic part by pressure molding the material by virtue of its viscous flow and optionally crystallizing or otherwise processing it to be semi-transparent or opaque. The glass material of the invention contains silicon oxide, magnesium oxide, aluminum oxide, and titanium oxide as main components. When silicon oxide, magnesium oxide, aluminum oxide, and titanium oxide are calculated as $SiO_2$, $MgO$, $Al_2O_3$, and $TiO_2$, respectively, the content of these components in the glass material, as expressed by percent by weight, is $SiO_2$ 40 to 65% by weight, $MgO$ 9 to 30% by weight, $Al_2O_3$ 8 to 31% by weight, and $TiO_2$ 6 to 15% by weight, preferably $SiO_2$ 40 to 55% by weight, $MgO$ 9 to 26% by weight, $Al_2O_3$ 9 to 31% by weight, and $TiO_2$ 7.5 to 13.5% by weight, more preferably $SiO_2$ 40 to 52% by weight, $MgO$ 11 to 26% by weight, $Al_2O_3$ 10 to 22% by weight, and $TiO_2$ 7.5 to 13.5% by weight.

By crystallizing, phase separating or otherwise processing a glass material of such composition to be semi-transparent or opaque, mainly high strength and superior aesthetic appearance are achieved as well as high productivity. The reason of limitation of the composition is described below in detail. With too low contents of $SiO_2$, vitrification is difficult, chemical durability is low, and high strength is not expectable. Too high contents of $SiO_2$ increase working temperature, prohibit debubbling, and are unlikely to ensure glass uniformity. With too low contents of $MgO$, a melt would have a higher viscosity enough to disturb working. With too high contents of $MgO$, vitrification is difficult and chemical durability is low. With too low contents of $Al_2O_3$, uniform precipitation of crystal grains is difficult upon crystallization. Too high contents of $Al_2O_3$ increase working temperature, prohibit debubbling, and are unlikely to ensure glass uniformity. Too low contents of $TiO_2$ prohibit uniform crystallization in the glass interior and allow preferential crystallization from the glass surface so that a crystal layer covers the surface to detract from aesthetic appearance and strength. With too high contents of $TiO_2$, molding at relatively low temperatures from the glass transition temperature to crystal precipitation becomes difficult because when glass material is heated from its glass transition temperature, crystallization takes place before a sufficient viscosity drop to enable molding occurs. Also subtle control of a degree of semi-transparency or opaqueness to provide aesthetic appearance as required for dental crowns becomes difficult.

While the content of the respective compounds as main components is limited to the above-defined range, the glass material of the invention also requires that the content of the respective compounds satisfy the following expression I.

$$\{100-(A+S+T)\}/S \geq 0.340, \quad \text{I:}$$

preferably $\{100-(A+S+T)\}/S \geq 0.375$, more preferably $\{100-(A+S+T)\}/S \geq 0.420$.

In expression I, A, S and T are contents in % by weight of $Al_2O_3$, $SiO_2$, and $TiO_2$, respectively. If A, S and T do not satisfy expression I, fluidity in the temperature range from the glass transition temperature to less than the liquidus temperature is insufficient and the benefits of the invention are lost. While expression I is empirically derived, it is believed that the limitation by expression I has the following contribution to a fluidity improvement. $Al_2O_3$ and $SiO_2$ are network-forming substances and increase the viscosity of glass. On the other hand, $TiO_2$ promotes crystallization. The numerator of expression I, that is, $100-(A+S+T)$ represents the amount of substances which improve the fluidity of glass or do not increase the viscosity of glass, such as MgO and other network-modifying substances. This amount divided by the amount of $SiO_2$, which is the denominator, can be used as an index indicative of the fluidity of glass.

In the glass material, the above-mentioned main components preferably occupy at least 80% by weight, more preferably at least 86% by weight. The benefits of the invention would be somewhat lost if the proportion of the main components is too low.

In addition to the main components, various auxiliary components are added, if desired, for the purposes of improving aesthetic appearance, increasing mechanical strength, matching the coefficient of thermal expansion with that of a mold, and improving fluidity.

As the auxiliary component, at least one of Ca, Ba, and Zn may be contained. Ca and Ba increase fluidity and lower working temperature. As compared with alkali metal elements, Ca and Ba have less detrimental influence on chemical durability. Also, since the addition of Ca facilitates precipitation of diopside grains, it contributes to an improvement in mechanical strength. Zn is added when it is necessary to increase a coefficient of thermal expansion. When these components are calculated as CaO, BaO, and ZnO, respectively, the sum of CaO+BaO+ZnO should preferably be up to 20% by weight, more preferably up to 15% by weight. Aesthetic appearance worsens if the total content is too high. More particularly, crystallization would take place from the surface of glass material if Ca and Ba contents are too high, and appropriate color tone as dental crowns and orthodontic parts would be lost if Zn contents are too high.

Also, at least one of noble metal elements, that is, Pd, Pt, Ag, Au, Re, Ru, Rh, and Ir may be contained as the auxiliary component. The addition of these noble metal elements improves aesthetic appearance and strength and allows the working time upon crystallization to be reduced, but has the problems of reproducibility and cost increase. The total content of noble metals should preferably be up to 1% by weight, more preferably up to 0.5% by weight. Appropriate color tone as dental crowns and orthodontic parts would be lost if the total content of noble metals is too high.

Also, at least one of Mn, Fe, Ni, and Ce may be contained as the auxiliary component. These elements are added in order to impart attractive color tone as dental crowns. When these elements are calculated as MnO, FeO, NiO, and $CeO_2$, respectively, the sum of $MnO+FeO+NiO+CeO_2$ should preferably be up to 2% by weight. Appropriate color tone as dental crowns and orthodontic parts would be lost if the total content of these elements is too high.

Also, at least one of alkali metal elements and phosphorus, that is, Li, Na, K, and P may be contained as the auxiliary component. The alkali metal elements are added for lowering the glass transition temperature and working temperature and also for matching of a coefficient of thermal expansion. Phosphorus is added for matching of a coefficient of thermal expansion and contributes to an improvement in aesthetic appearance. When these elements are calculated as $Li_2O$, $Na_2O$, $K_2O$, and $P_2O_5$, respectively, the sum of $Li_2O+Na_2O+K_2O+P_2O_5$ should preferably be up to 5% by weight, more preferably up to 2% by weight. Since alkali metal elements and P detract from chemical durability, it is most preferred to exclude these elements.

Also, B may be contained as the auxiliary component. Boron is added for matching of a coefficient of thermal expansion. When B is calculated as $B_2O_3$, the content of $B_2O_3$ should preferably be up to 5% by weight, preferably up to 3% by weight. Since boron detracts from chemical durability, it is most preferred to exclude this element.

Also, Zr may be contained as the auxiliary component. Zirconium contributes to an improvement in aesthetic appearance. When Zr is calculated as $ZrO_2$, the content of $ZrO_2$ should preferably be up to 5% by weight, preferably up to 3% by weight. Too high contents of $ZrO_2$ inhibit vitrification.

Raw materials of the main components are commonly available as oxides although nitrides may be partially used. The auxiliary components may be added as either elements or compounds. Compounds of auxiliary component elements include oxides, nitrides, chlorides, nitrates, and sulfates. It is believed that where nitrides are used as part of the raw materials, nitrogen atoms are contained in the glass as substituting for oxygen atoms. It is excluded that nitrides are contained as short fibers and whiskers in the glass material of the invention. With nitrogen contained, the content of $Si_3N_4$ is preferably up to 4% by weight when nitrogen is calculated as $Si_3N_4$. Too high nitrogen contents would lead to too high hardness and worsen the reproducibility of composition because a nitrogen composition variation is likely to occur during manufacture.

The glass material of the invention may contain auxiliary components other than the above-mentioned ones, but is substantially free of fluorine. This is because fluorine worsens the reproducibility of composition, precludes molding, deteriorates the furnace, and is hazardous to the human body as previously mentioned. To be substantially free of fluorine means that no fluorides are used as glass-forming raw materials.

When the glass material of the invention contains auxiliary components, the compositional ratio of the respective compounds as the main components should satisfy the following expression II:

$$(S+M)/4 > 100-(S+M+A+T), \qquad \text{II:}$$

preferably, $(S+M)/5 > 100-(S+M+A+T)$.

In expression II, A, S and T are as defined for expression I, and M is a content in % by weight of MgO. Expression II is empirically derived. Although the crystallization mechanism in the compositional system of the glass material according to the invention is not well understood, the addition of auxiliary components basically inhibits phase separation and as a result, uniform crystallization becomes difficult, high strength is lost, and aesthetic appearance is exacerbated. In phase separate glass of an Si—B—Na—O system, for example, phase separation is retarded as the Na content increases. It is believed that like the phase separate glass of this system, the addition of auxiliary components retards phase separation in the glass material of the invention. It is believed that in the glass material of the invention, an Si—Mg—O network greatly contributes to the formation of separate phases and auxiliary components to retard phase separation from occurring by scissoring this network. Therefore, expression II is empirically determined such that the right side of expression II, that is, the content of auxiliary components is less than a fraction of $(SiO_2+MgO)$. If $(S+M)/4 \leq 100-(S+M+A+T)$, then uniform crystallization is precluded.

In general, glass allows more or less crystal grains to precipitate between the glass transition temperature (Tg) and the liquidus temperature. In this temperature range, the fluidity of glass largely varies depending on the amount of grains precipitated. The viscosity of glass gradually declines as temperature rises from Tg toward the liquidus. In the case of glass materials which are likely to precipitate grains, the viscosity rises with the progress of crystallization above a certain temperature. Therefore, glass materials having a strong grain precipitating tendency will rapidly crystallize at temperatures below the softening point (viscosity $4.5 \times 10^7$ P) according to Littleton, and cannot be fully deformed or molded below the liquidus temperature. If the grain precipitating tendency is weak, on the other hand, a vitreous state is maintained up to higher temperatures, ensuring greater fluidity and better moldability. However, a higher temperature and a longer time are required to precipitate grains, giving rise to several problems with respect to the price of a furnace, working time, reaction with a mold and the like.

From these considerations, it is desirable that when the glass material has a viscosity $\eta$ (P), the material can maintain for at least 7 minutes, more preferably at least 10 minutes, most preferably at least 15 minutes the state that $\log\eta$ is up to 7.6 at a heating rate of 5° C./min. in the heating step from the glass transition temperature to 1,000° C. Also preferably, the minimum of $\log\eta$ is up to 7.0, more preferably up to 6.7 in the heating step from the glass transition temperature to 1,000° C. Moreover, when a cylindrical glass material is longitudinally compressed under an initial pressure of 1.8 MPa and then heated from its glass transition temperature to 1,000° C. at a rate of 5° C./min. while being compressed under a certain load, the material is preferably deformable or shrinkable at least 85%, more preferably at least 90% in the pressure applied direction. Since the area of the pressure receiving surface of glass material is expanded by pressure application, the pressure force per unit area decreases when the material is compressed under the fixed load. A punch used for compression should have a greater pressure applying surface than the pressure receiving surface of glass material at the end of deformation. The glass material of the invention can be given such fluidity and moldability by selecting its composition from the above-defined range.

It is noted that the glass material of the invention has a glass transition temperature of about 630° to about 770° C. although it varies with a particular composition.

The glass material which can be molded and crystallized at 1,000° C. or lower has the advantage that it avoids the problem associated with high temperatures of 1,050° C. or higher that reaction begins between glass and a dental investment compound used as a mold and investment compounds themselves are denatured to detract from strength especially when phosphate and cristobalite investment compounds are used.

The shape and dimensions of glass material may be suitably determined in accordance with a particular application. Readily moldable shapes are preferred, for example, frustoconical, cylindrical and spherical shapes are preferred for the manufacture of artificial dental crowns. To prevent entry of bubbles during molding, to prevent lowering of mechanical strength, and to produce a homogeneous molded body, a single piece of glass material is preferably used in the manufacture of a single molded body. Differently stated, it is recommended to avoid a plurality of glass material pieces or glass powders being integrally joined during molding. However, two or more glass material pieces may be used as part of the invention if necessary.

It is noted in the present invention that a flux or plasticizer need not be added to glass material for softening purposes upon pressure molding.

Preparation method

According to the present invention, a living tissue replacement is prepared by pressure molding glass material, then heat treating it to be semi-transparent or opaque through crystallization or the like and optionally, machining it. The method of preparing a living tissue replacement according to the invention is described with reference to FIG. 1.

The glass material is prepared by melting a raw material and quenching the melt. For melting, the raw material is heated in a crucible of platinum, quartz or alumina preferably for about 5 minutes to 20 hours, more preferably about 10 minute to about 2 hours. The melting temperature which depends on the composition is generally above 1,400° C. or higher. The raw material is a mixture of oxides or substances capable of forming oxides upon melting, for example, carbonates, bicarbonates and hydroxides. Upon heating, raw material components react with each other to form a composite oxide. Melting is generally done in air. The quenching method is not critical insofar as amorphous glass is obtained at the end of quenching. For example, the melt is poured to sheet iron, carbon, water or mold. The mold may be made of dental investment compounds such as cristobalite, calcium phosphate or the like.

For glass homogenization, a melting→cooling→crushing→remelting process may be repeated or high-frequency induction heating may be employed.

The thus prepared amorphous transparent glass material is converted into a semi-transparent or opaque living tissue replacement, preferably by any of the procedures shown in FIGS. 1(a) to 1(c).

The procedure shown in FIG. 1(a) includes the steps of heat treating the glass material for nucleation or phase separation, pressure molding it at a temperature equal to or above its glass transition temperature, and processing it to be semi-transparent or opaque. Most often, the living tissue replacement of the invention is made semi-transparent or opaque by crystallizing the glass material. It is noted that in some cases, no definite peak is observed on X-ray diffraction even after the glass material is made semi-transparent or opaque. Such a glass material is believed to be emulsified and turbid due to precipitation of undetectable very fine grains and/or phase separation and even in such a case, it can be utilized as a living tissue replacement in the practice of the invention. A glass material in which emulsified turbidity due to precipitation of undetectable very fine grains and/or phase separation and crystallization detectable by X-ray diffraction have simultaneously occurred can also be utilized as a living tissue replacement. Where it is unnecessary to be semi-transparent or opaque, the glass material as pressure molded may be used as a living tissue replacement while it is transparent.

It is noted that heat treatment for semi-transparency or opaqueness is carried out after pressure molding in FIG. 1(a) although the material can be made semi-transparent or opaque by the heat applied during pressure molding. In FIG. 1(a), the heat treatment for nucleation or phase separation is designated as primary heat treatment and the heat treatment for semi-transparency or opaqueness is designated as secondary heat treatment.

The procedure shown in FIG. 1(b) carries out the secondary heat treatment after pressure molding while omitting the primary heat treatment. Also in this procedure, the material can be made semi-transparent or opaque by the heat applied during pressure molding without carrying out independent secondary heat treatment.

In the procedure shown in FIG. 1(c), primary and secondary heat treatments are successively carried out after pressure molding.

Although it is not impossible to carry out pressure molding after the glass material is made semi-transparent or opaque, this procedure is undesirable because of extremely low efficiency. Note that some glass materials having a special composition can be pressure molded in a relatively simple manner after they are made semi-transparent or opaque;

In these procedures, the primary heat treatment is optionally effected in order to allow for uniform crystallization of glass. Although a certain composition of glass material fails to provide a desired color tone and sufficient strength due to abnormal crystal growth, nucleation treatment prior to crystallization ensures uniform crystallization. Since the primary heat treatment prior to crystallization ensures uniform crystallization, primary heat treatment is advantageously used for the manufacture of dental crowns whose outer appearance is of importance. The primary heat treatment is also effective for reducing the time taken in crystallization. The conditions of primary heat treatment are not critical although heat treatment is preferably effected near a temperature where nucleation or phase separation occurs, especially in the range of 600° to 850° C. for about 30 minutes to about 50 hours. If the nucleation or phase separation temperature is close to the crystallization temperature, primary heat treatment may be omitted without substantial influence. Also, if the passage time across the temperature where nucleation or phase separation occurs is prolonged by reducing the heating rate during the secondary heat treatment, there is obtained a living tissue replacement having aesthetic appearance as obtained when the primary heat treatment is independently carried out.

The temperature during pressure molding in the respective procedures of FIG. 1 is equal to or above the glass transition temperature of glass material, preferably in the temperature range at which molding is possible under a pressure of up to 5 MPa. In order to take advantage of the viscous flow of glass during pressure molding, heating is preferably carried out such that the viscosity of glass material and its change are as previously described. Since crystallization of glass material proceeds even during molding depending on a molding temperature, the molding temperature is properly determined such that the crystallinity may fall within a desired range. The temperature varies with the time taken for molding and may be determined by experiments.

The glass material can be molded, for example, by placing it in a mold and pressing it by a punch. The mold and punch may be made of dental investment materials based on cristobalite and phosphate cristobalite, alumina and zirconia. The mold and punch may be prepared with the ordinary skill of dental technicians.

The glass material may be heated by placing it in a pre-heated mold or by placing it in a mold and introducing the mold into a furnace. After the glass material has been heated to the predetermined temperature, it is subject to pressure molding. A hot press technique may be used for heating and pressing purposes. In an alternative technique, once heated, the mold is taken out of the furnace and a pressure force is then applied. This technique is effective for improving productivity because a plurality of molds each loaded with glass material can be concurrently heated in the furnace. Application of pressure force to the glass material may be initiated either before or after the maximum temperature during molding is reached. The former is advantageous in shortening the molding step because molding begins at the same time as the glass material softens. If a necessary amount of deformation is achieved before the maximum temperature is reached, compression may be interrupted at that point of time, which contributes to a further time saving. The latter ensures homogeneity after molding. Since a pressure force is applied subsequent to a glass viscosity drop, the mold is prevented from fracture. A pressure force is maintained until the glass material has been deformed to faithfully reflect the mold cavity, often for about 5 to 20 minutes although the exact time varies with press means and temperature.

No particular limit is imparted to the pressing technique during molding. Since the glass material can be molded under a low pressure of up to 5 MPa, especially up to 0.3 MPa, the invention eliminates a need for special press means and enables molding by merely using a hand press or weight, for example. In the case of a weight, the mold is heated with the weight rested on the punch. Then the weight descends as the glass material lowers its viscosity. The completion of molding can be detected by the termination of downward displacement of the weight. Also, when a pressure force is applied by a press machine with a constant crosshead speed maintained, the completion of molding may be determined in terms of crosshead displacement or pressure increase.

FIGS. 2 to 5 illustrate exemplary pressure molding procedures. An apparatus for shaping a living tissue replacement by pressure molding includes a mold 2 and a punch 4. The mold 2 includes a molding cavity 21 and a bore 23 which receives the punch 4 and is connected for fluid communication to the cavity 21 through a sprue 22. A frame 5 is an outer frame which is used when the mold 2 is cast. A buffer 6 lined inside the casting frame 5 is to accommodate expansion of the mold material. Often the casting frame 5 is an iron ring, and the buffer 6 is an asbestos ribbon. The molding cavity 21, sprue 22 and bore 23 are defined by a conventional lost wax process or the like. A block of glass material 3 is placed in the bore 23 and compressed by the punch 4 in the arrow direction. Since the glass material 3 has been heated to a predetermined temperature and thus has a low viscosity upon compression, the applied pressure causes the glass material to flow into the cavity 21 through the sprue 22 where it deforms faithfully to the cavity 21 to assume the dental crown shape.

Figure 3:
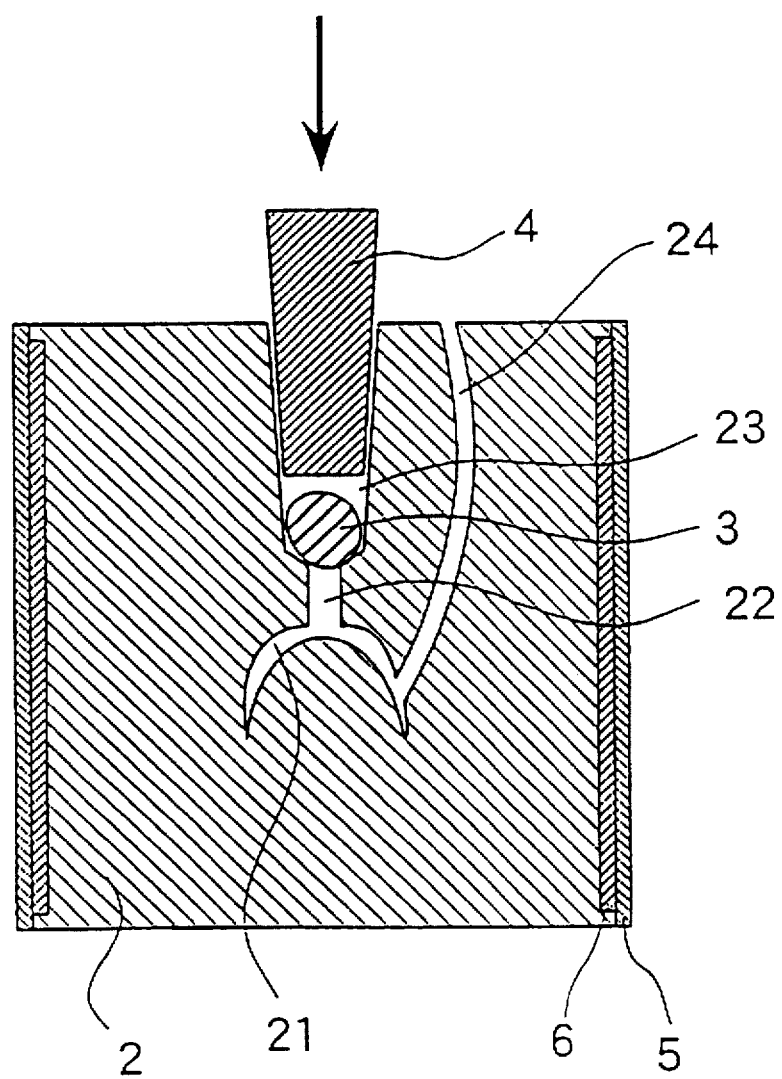
FIG. 3 illustrates one example of a pressure molding step.

In the embodiments wherein the bore 23 has a tapered inner surface as shown in FIGS. 2 and 3, the bore inner surface is inwardly tapered, preferably at a gradient of up to 1/5, more preferably up to 1/15. In the preferred embodiment shown in FIG. 4, the bore 23 has an inner surface which extends substantially parallel to the pressure application direction. The bore with a slightly tapered or straight inner surface defines with a similarly tapered or straight punch 4 a minimal gap which is effective for preventing back flow of the softened glass material 3 therethrough. This saves the amount of glass material to be loaded. The bore 23 is generally circular in cross section (taken perpendicular to the pressure application direction) although it may also be ellipsoidal or polygonal.

Figure 4:
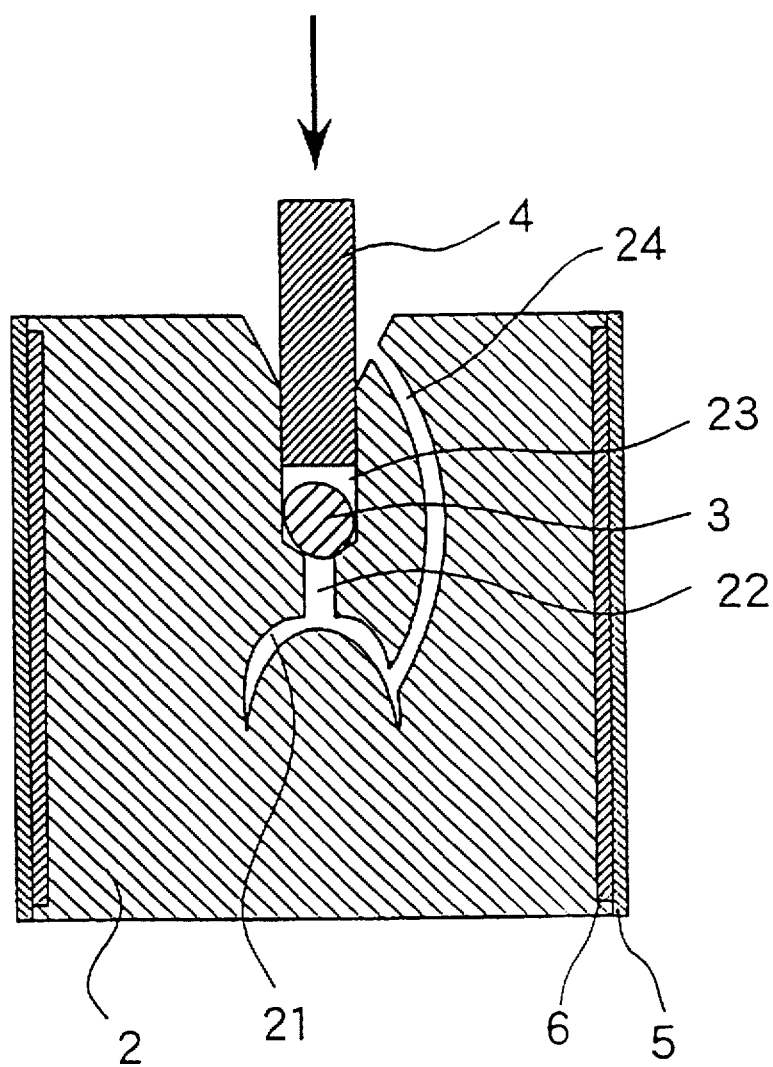
FIG. 4 illustrates one example of a pressure molding step.
Figure 5:
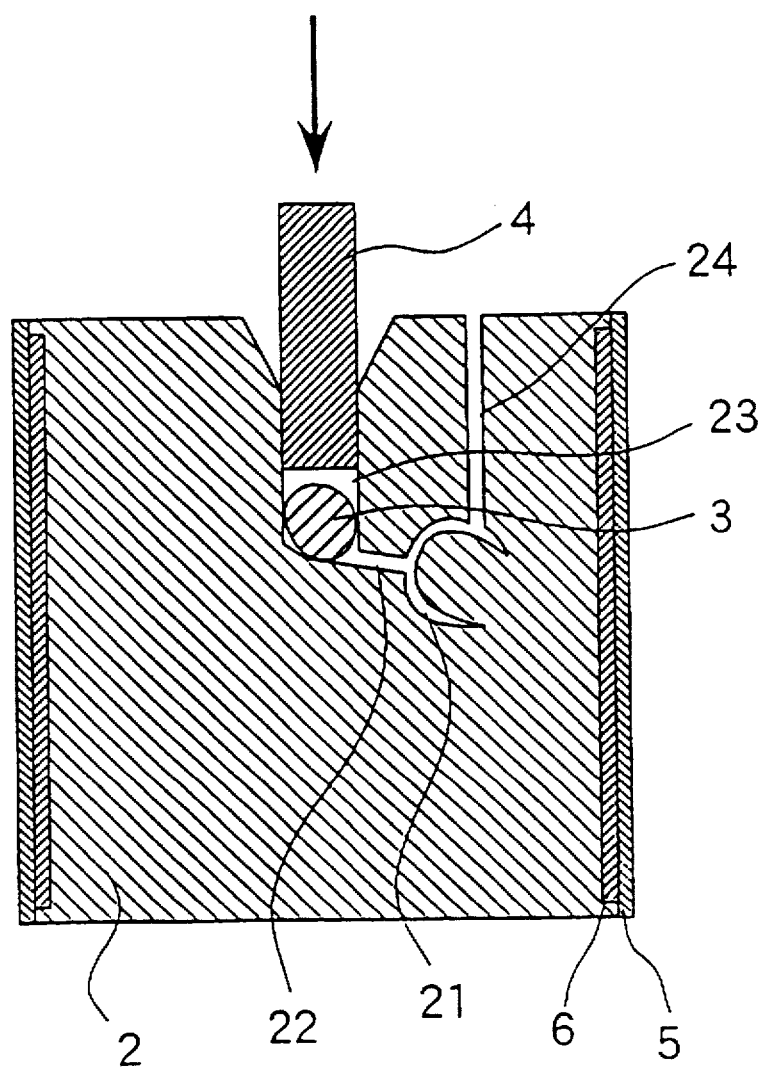
FIG. 5 illustrates one example of a pressure molding step.

Preferably the mold 2 is provided with a vent or runoff path 24 connected in fluid communication with the molding cavity 21 as shown in FIGS. 3 to 5. The vent 24 allows part of the glass material to run off upon pressure application, thereby facilitating to fill the cavity 21 with the glass material and to produce a molded part faithful to the cavity under a relatively low pressure. The vent 24 is also effective for preventing application of excess pressure to the mold upon pressure application, thus preventing the mold 2 from cracking. As a result, the percentage of deficient parts is drastically reduced. The diameter and cross-sectional shape of the vent 24 may be suitably determined depending on the volume and shape of the molding cavity 21. More than one vent 24 may be provided. Often the vent 24 is defined by a conventional lost wax process or the like. In the illustrated embodiments, the vent 24 opens to the exterior of the mold 2. Since conventional dental molds are well air permeable, it is unnecessary to discharge air in the molding cavity 21 through the vent 24. Then the vent 24 need not open to the exterior of the mold 2. The vent 24 is communicated to the mold exterior in the illustrated embodiments because such a through-vent is easier to define by a lost wax process.

The sprue 22 connecting the molding cavity 21 and the punch-receiving bore 23 is preferably inclined with respect to the pressure application direction as shown in FIG. 5. The inclined sprue 22 facilitates to channel the glass material into the cavity 21 and to produce a molded part faithful to the cavity under a relatively low pressure and prevents the mold 2 from cracking upon pressure application. The angle of inclination relative to the pressure application direction is not particularly limited although it is desired that when the inlet and outlet of the sprue 22 are projected to a plane perpendicular to the pressure application direction, their projected images do not overlap. As long as the inlet and outlet of the sprue 22 are offset in this relationship, the sprue 22 need not be a straight one as shown in FIG. 5, with a curved sprue acceptable.

The sprue 22 preferably has a cross-sectional shape corresponding to the shape of the molding cavity 21. When it is desired to mold an artificial dental crown for the incisor as in the illustrated embodiment, the sprue 22 has a minor diameter/major diameter ratio of about 1:7 in cross section in compliance with the flatness of the incisor. Then a molded body of a shape highly faithful to the molding cavity 21 can be produced under a relatively low pressure. The sprue 22 need not have a constant cross-sectional area from the inlet to the outlet and may vary in area.

Figure 6:
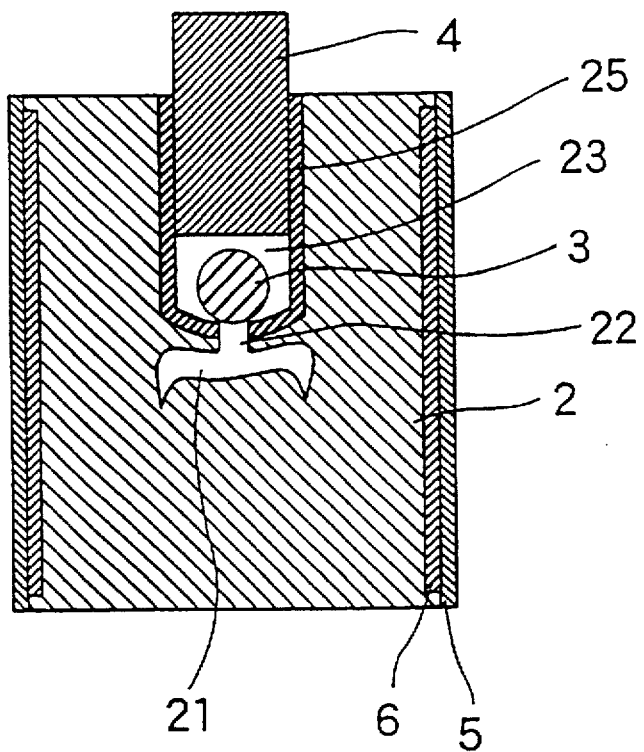
FIG. 6 is a cross-sectional view of a molding apparatus having a high strength liner 25 disposed inside a punch insertion bore 23.
Figure 7:
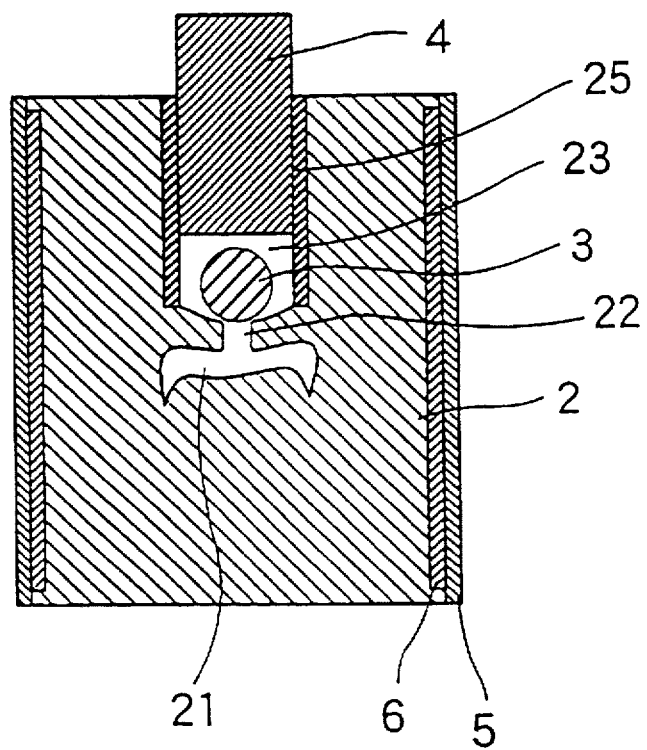
FIG. 7 is a cross-sectional view of a molding apparatus having a high strength liner 25 disposed inside a punch insertion bore 23.

In a further preferred embodiment, the mold 2 includes a liner 25 which covers at least a portion of the inner surface of the punch-receiving bore 23 as shown in FIGS. 6 and 7. The liner 25 is made of a high strength material having a higher compression strength than the material of the mold 2.

The bore 23 is lined with the high strength liner 25 at its inner surface for preventing rupture of the molded part. Since pressure is applied to the mold 2 during pressure molding, the mold 2 can be cracked. If the glass material penetrates into such cracks, there is a likelihood that the molding cavity 21 be short of the glass material. Still worse, if cracks reach the cavity 21, the resulting molded part has burrs. Such cracking can be avoided by increasing the strength of the mold with a concomitant failure of the molded part upon withdrawal from the mold. This is because the molded part is generally withdrawn from the mold by applying an external force to the mold to form cracks therein and removing the mold material fragments. To destroy the high strength mold, a greater force must be applied to the mold so that the inside molded part can be damaged thereby. Then in the embodiments shown in FIGS. 6 to 8, the bore 23 is provided with the high strength liner 25 on the inner surface and the mold 2 itself is made of a material having relatively low compression strength, which not only prevents the mold from cracking under the molding pressure, but also ensures that the mold is readily destroyed without causing damage to the inside molded part upon withdrawal of the molded part from the mold.

Figure 8:
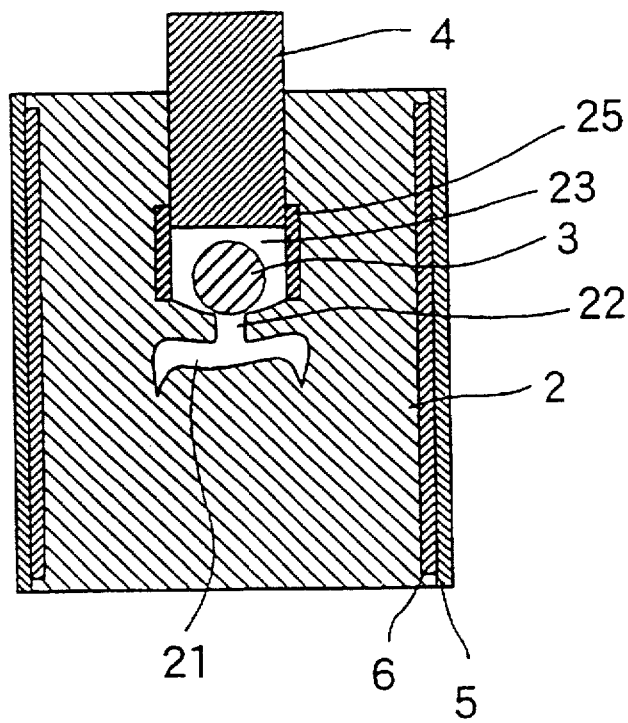
FIG. 8 is a cross-sectional view of a molding apparatus having a high strength liner 25 disposed inside a punch insertion bore 23.

Although the high strength liner 25 is preferably extended over the entire inner surface of the bore 23 as shown in FIG. 6, it is only required that the liner 25 cover a portion of the bore inner surface, especially that portion of the bore inner surface which comes in contact with the glass material 3 during pressure molding. Since it is rather difficult and expensive to apply high strength material to the shape shown in FIG. 6, it is acceptable that the high strength material or liner be not applied near the bottom of the bore 23 as shown in FIGS. 7 and 8.

The high strength liner is generally about 0.1 to about 3 mm thick although the thickness is not critical and may be suitably determined by taking into account the type of high strength material and molding pressure.

Figure 9:
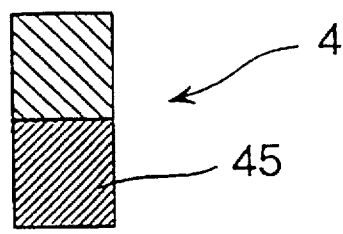
FIGS. 9(a), 9(b) and 9(c) are cross-sectional views of a punch 4 which is partially formed of a high strength material 45.
Figure 9:
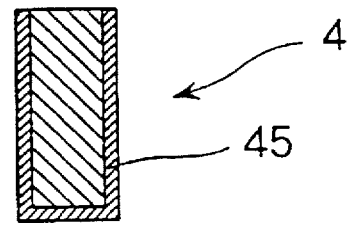
Figure 9:
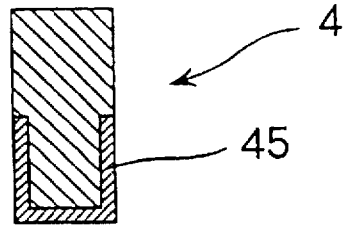

The punch 4 receives only compression stress in a substantial sense. Then even when the punch 4 is made of a material having relatively low compression strength, its failure is less probable. However, it is preferred that the punch 4 is at least partially formed of a reinforcing or high strength material 45 having higher compression strength than the material of the mold 2 as shown in FIGS. 9(a), 9(b) and 9(c). The high strength material or cover 45 prevents the punch 4 from such failure as cracks and fracture. The reinforcement or cover 45 of high strength material forms or covers at least a portion of the surface of the punch 4 opposed to the bore inner surface, especially that portion of the punch surface which comes in contact with the glass material 3 during pressure molding. Since there is a tendency that some glass deposits remain on the punch 4 after molding, it is a common practice to replace the punch 4 by a new one on every molding operation. Then the embodiment wherein only a portion of the punch 4 is made of the high strength material as shown in FIG. 13 is cost effective because the punch can be manufactured at a lower cost by reducing the amount of the high strength material which is expensive than the low strength investment materials. The high strength cover 45 in the embodiments of FIG. 9 may have a thickness similar to that of the high strength liner 25 associated with the punch-receiving bore 23.

The material of which the mold 2 is made preferably has a compression strength of up to 20 MPa, more preferably up to 15 MPa and preferably at least 2 MPa, more preferably at least 4 MPa at the end of pressure molding. If the compression strength of the mold material is too high, the probability of molded part failure would become high for the above-mentioned reason. If the compression strength of the mold material is too low, the mold would be broken during molding even when the high strength liner is provided.

The compression strength of the mold material is defined herein as that after compression molding because the mold is concurrently heated during pressure molding and the compression strength depends on this heating. It is possible to facilitate withdrawal of the molded part from the mold by immersing the mold in water for softening and in this case, the compression strength is that of the mold which has been immersed in water.

Also preferably the high strength material has a compression strength of at least 15 MPa, more preferably at least 30 MPa. With a compression strength below the limit, provision of the reinforcing material would be meaningless. No upper limit need be imposed on the compression strength of the high strength material. Often a material having a compression strength of up to 2,000 MPa is preferably used for availability and ease of shaping.

The compression strength used herein is measured according to JIS R 1608 when the mold material and high strength material are ceramics. More particularly, five cylindrical samples of 12.5 mm in diameter and 5 mm in height are molded from the material and measured for compression strength at a crosshead speed of 0.5 mm/min. For a metallic reinforcing material, the compression strength is given as the value at which an object on test is broken when the same compression strength measuring procedure as used for the ceramics is carried out.

The material having relatively low compression strength of which the mold 2 is made may be suitably selected from dental investment materials, for example, cristobalite and phosphate system cristobalites such as calcium phosphate cristobalite as well as gypsum, with the cristobalite being preferred. Cristobalite may be softened, further softened by immersing in water, or smoothed on surface. The material for the high strength liner 25 or cover 45 is not particularly limited and may be suitably selected by taking into account its relationship to the compression strength of the mold material, preferably from metal and ceramic materials. Ceramic materials are especially preferred because the heat during pressure molding can cause metals to react with the glass material to undesirably color the glass material. Preferred examples of the metal are stainless steel and iron while preferred examples of the ceramic include alumina, silicon carbide, zirconia, and zeolite. Ceramic mixtures such as mixtures of various porcelains and refractories (e.g., feldspar-quartz-kaolin systems) are also preferred. Further phosphate system cristobalites, dental refractories and gypsum are acceptable.

Any desired method may be used to form the liner 25 and reinforcement or cover 45 of high strength material although the following method is often used.

Figure 10:
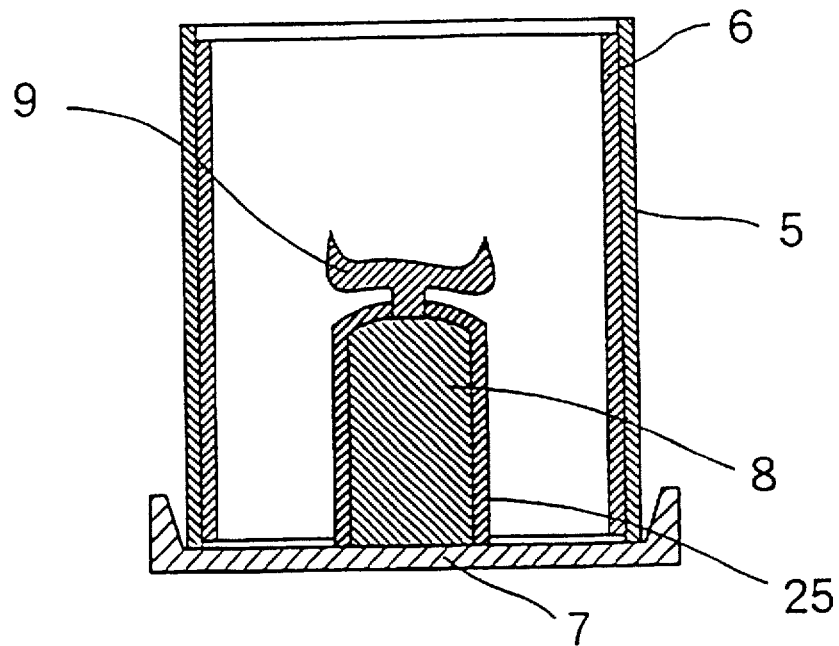
FIG. 10 is a cross-sectional view illustrating a method for applying a high strength liner to the inner surface of a punch insertion bore.

FIG. 10 illustrates how to form the mold 2 by a lost wax process. The casting frame 5 and buffer 6 are rested on a support 7. A shape 8 of silicone rubber or the like for forming the punch-receiving bore is placed within the frame 5. A high strength material is applied to the surface of the shape 8 to form the liner 25. On the shape 8 is located a wax shape 9 for forming the sprue and cavity. In this state, a mold material such as an investment compound is cast into the frame 5 followed by ordinary steps of a conventional lost wax process.

Figure 11:
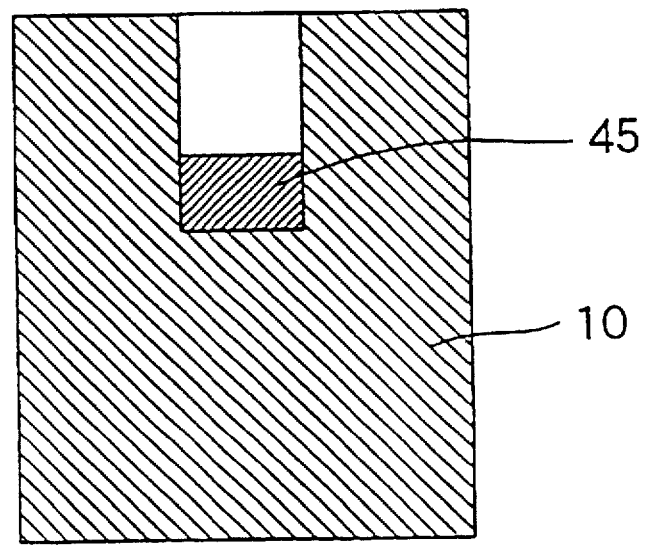
FIG. 11 is a cross-sectional view illustrating a method for preparing a punch which is partially formed of a high strength material.
Figure 14:
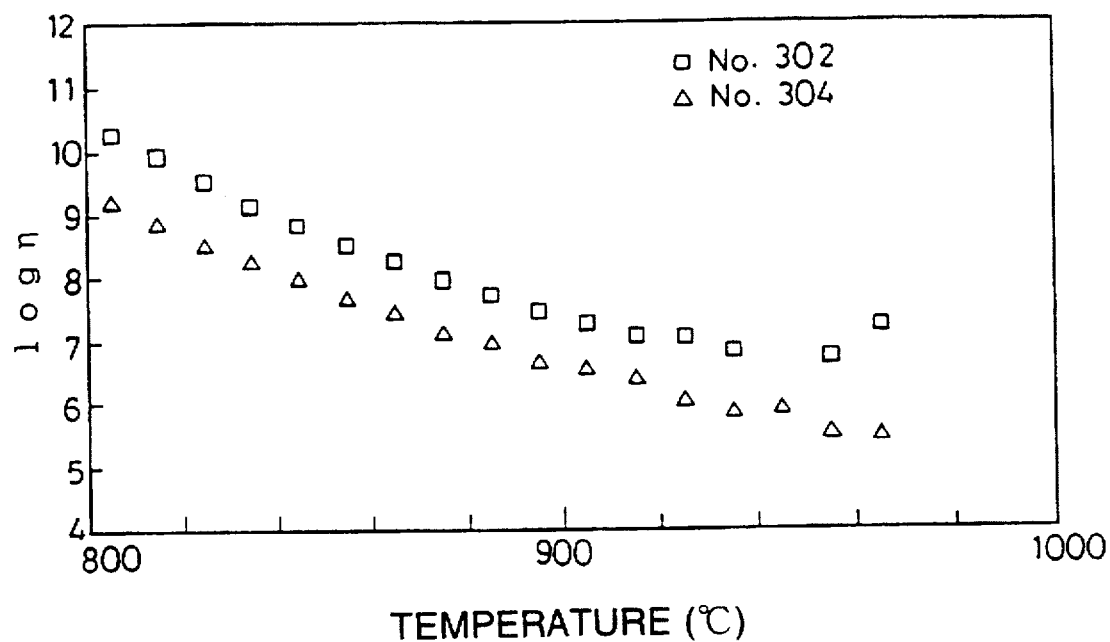
FIG. 14 is a graph showing a viscosity change of glass material during a heating step.
Figure 15:
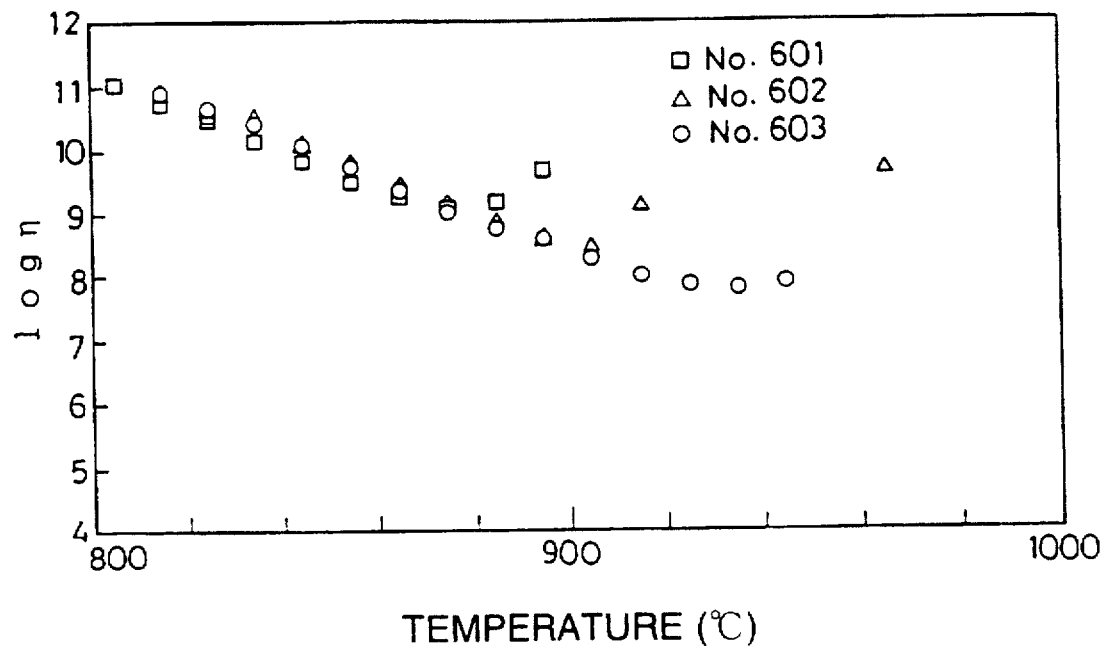
FIG. 15 is a graph showing a viscosity change of glass material during a heating step.
Figure 16:
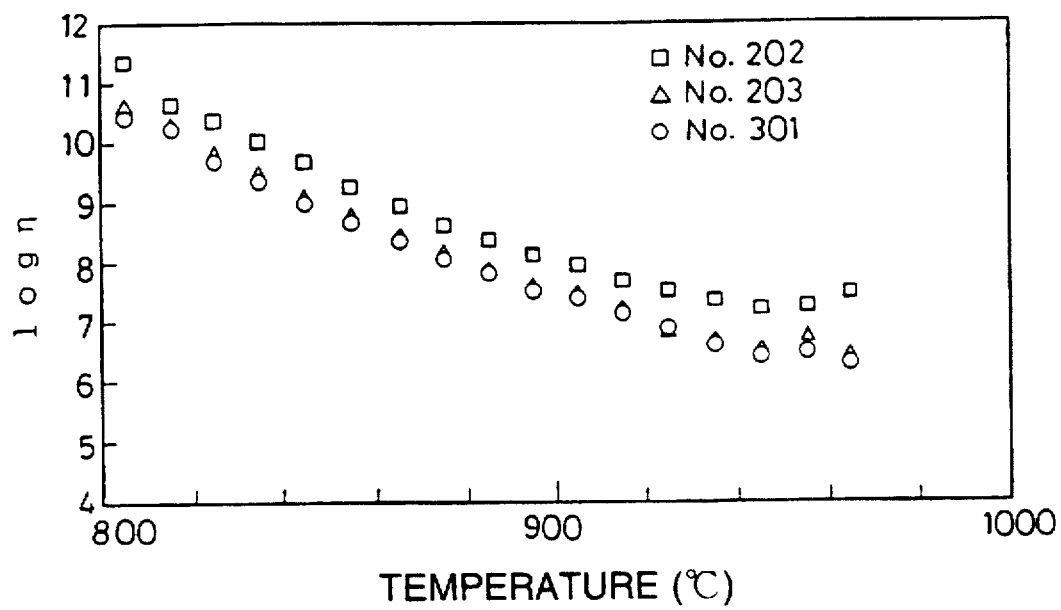
FIG. 16 is a graph showing a viscosity change of glass material during a heating step.
Figure 17:
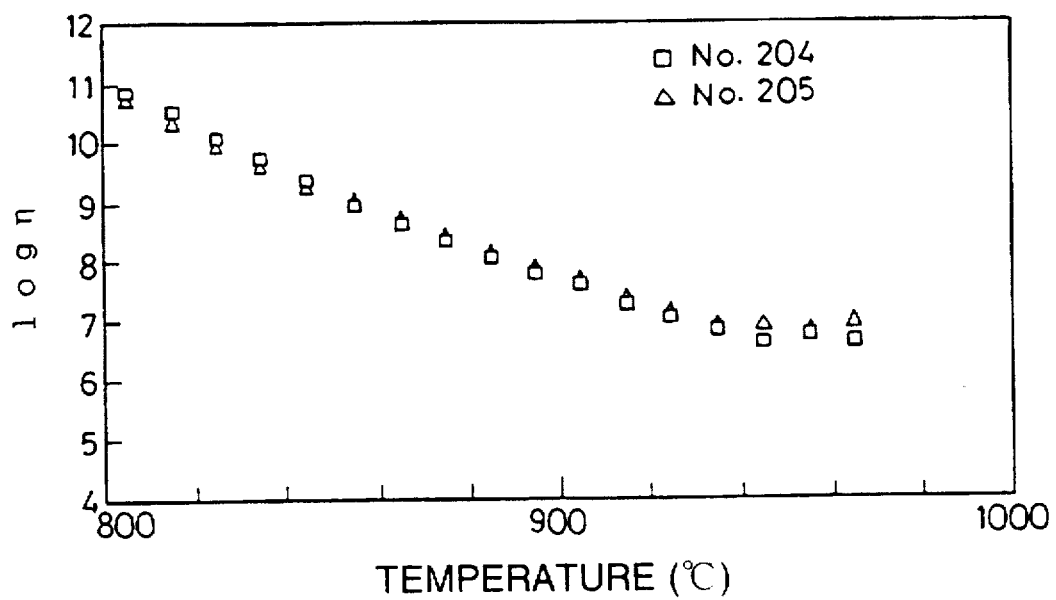
FIG. 17 is a graph showing a viscosity change of glass material during a heating step.
Figure 18:
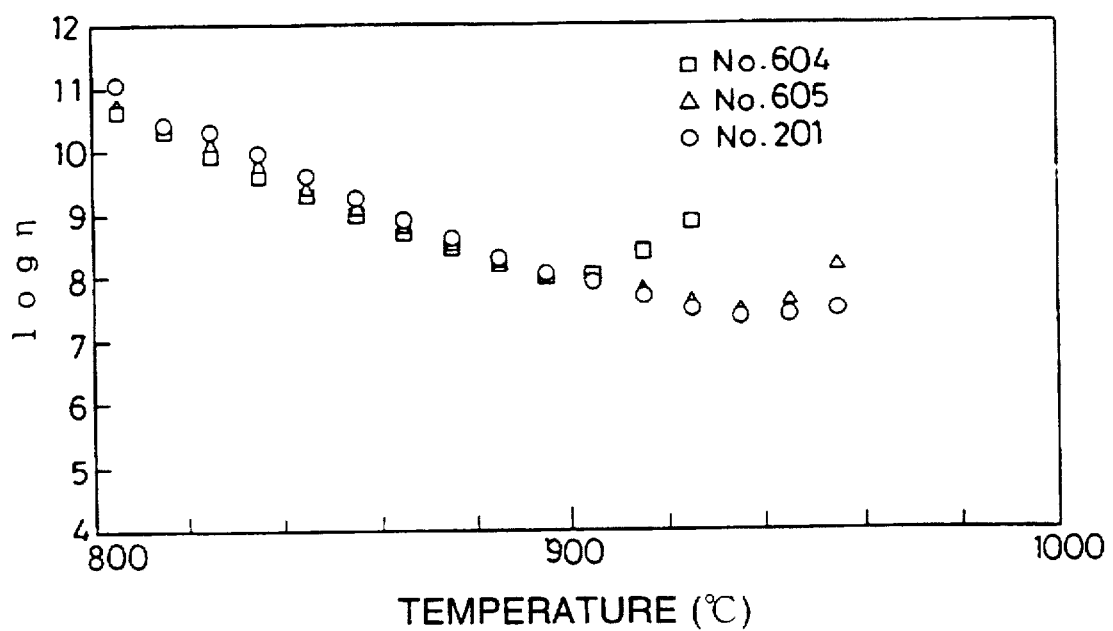
FIG. 18 is a graph showing a viscosity change of glass material during a heating step.

The punch 4 including a lower portion in the form of the high strength material reinforcement 45 is prepared, as shown in FIG. 11, by placing a high strength material 45 in a cavity of a punch-forming mold 10 of silicone rubber or the like, casting a punch material such as an investment compound thereon, and removing the mold 10.

After the glass material is pressure molded by the living tissue replacement molding apparatus mentioned above, the molded part is allowed to cool down inside or outside the furnace. If desired, the molded part is slowly cooled at a controlled rate. The molded part can be taken out of the mold by an ordinary technique commonly employed by the dental technician.

The glass material of the invention can be made substantially semi-transparent or opaque at about 850° to 1,000° C. The substantially opaque glass material means that it has such a degree of opaqueness that when a glass piece of 2 mm thick whose surfaces opposed in thickness direction are mirror polished is placed on printed lines of 2 mm wide, the lines cannot be visually identified through the glass piece. When the glass material is semi-transparent, the presence of the lines is acknowledged, but the edge of the lines is indefinite. The degree of opaqueness may be suitably determined as desired. The temperature holding time in the secondary heat treatment is not particularly limited and may be suitably determined such that a desired degree of semi-transparency or opaqueness is available although it is generally up to 10 hours, with a holding time of up to 1 hour being acceptable. It is acceptable to cool the material immediately after arrival at the predetermined temperature without holding at the temperature.

Where crystallization proceeds from the proximity of the surface of glass material, a region having higher crystallinity can be present near the surface of glass material after crystallization. The thickness of this region from the surface should preferably be up to 3 µm. It is, however, preferred that crystallization proceeds uniformly and such a region is substantially absent.

Where the secondary heat treatment follows the pressure molding step, it is recommended to subject the molded part to the secondary heat treatment without cooling because of improved productivity.

A percent change of density upon treatment of glass material for semi-transparency or opaqueness, which is given as {(density after semi-transparent or opaque treatment)−(density before semi-transparent or opaque treatment)}/(density before semi-transparent or opaque treatment), is preferably −5% to +3%. The procedures of making glass semi-transparent or opaque generally include crystal precipitation, phase separation to be turbid, and phase separation followed by crystallization of the resultant phase. If the crystalline phase has a greater density than the vitreous phase as a result of crystal precipitation and phase separation followed by crystallization, voids can be formed within the glass and/or the glass shrinks. In the former case, glass strength lowers. In the latter case, dimensional precision is affected. The glass material of the invention can avoid these problems because by properly selecting a composition, the change of density upon treatment for semi-transparency or opaqueness can be minimized as mentioned above.

It is noted that expansion can occur upon heat treatment and a problem of dimensional precision can occur in this case. Then an increment by expansion may be machined which does not create a significant problem as does shrinkage. Particularly when treatment for semi-transparency or opaqueness is carried out within the mold after molding, a shift of dimensional precision caused by a difference in density between phases creates no significant problem.

The crystals formed in the glass material of the invention are not particularly limited. The crystals formed are different depending a composition and difficult to identify. Examples of the formed crystals which can be identified include magnesium titanate, enstatite, β-quartz, magnesium aluminotitanate, rutile, gahnite, diopside, sapphirine, and petalite.

At the end of crystallization, the mean grain size is not critical although it is generally up to 100 µm, preferably up to 10 µm, more preferably up to 1 µm. With a larger grain size, high strength is seldom obtained. The grain size may be determined by scanning electron microscope (SEM) and X-ray small angle scattering.

In the present invention, the glass transition temperature, softening point, crystallization temperature and nucleation or phase separation temperature may be determined by differential thermal analysis and measurement of a coefficient of thermal expansion.

Living tissue replacements may be shaped solely by pressure molding of glass material as mentioned above although the molded part resulting from pressure molding may be further machined to form a living tissue replacement. The machining step is advantageous in producing a living tissue replacement of complex shape to which a mold cavity can be precisely molded with difficulty or in producing a living tissue replacement which requires very high dimensional precision. If the molded part has a shape and size approximate to the final living tissue replacement, machining can be completed within a short time and the waste of glass material can be reduced. The type of machining is not particularly limited and may be any of machining using drills of high hardness material such as diamond and carborundum, lathe machining and the like.

For use as an artificial dental crown, the living tissue replacement of the invention has not only good aesthetic appearance, but also water resistance and acid resistance so that it is least deteriorated even when exposed in the oral cavity, and thus has a very long endurance time.

Although the invention has been described as being mainly applied to artificial dental crowns, the invention is equally applicable to other living tissue replacements, for example, artificial bones such as ossiculum, bone screws, percuteneous terminals, blood vessels, and air tubes. Such examples of the living tissue replacement are illustrated in FIG. 12. FIG. 12(a) is an artificial vertebra body, FIG. 12(b) is an artificial intervertebral disk, FIG. 12(c) is an artificial ilium, FIG. 12(d) is an artificial air tube, and FIG. 12(e) is a bone screw.

Next, the method of preparing an orthodontic part according to the invention is described. FIGS. 13(a), 13(b), 13(c), and 13(d) illustrate exemplary orthodontic parts to which the invention is applicable. The orthodontic part is basically prepared by the same method as the above-mentioned living tissue replacement. Since the orthodontic part is generally desired to have higher transparency, the primary heat treatment in FIG. 1 is generally omitted, and the treating time of secondary heat treatment is reduced or the heat during pressure molding is utilized instead of independent secondary heat treatment.

EXAMPLE

Examples of the present invention are given below by way of illustration.

Glass material

Glass ingots were prepared by weighing compounds and metals in powder form as shown in the following Tables so as to provide relative contents as shown in the Tables, forming a homogeneous glass melt by a re-melting method, and casting the glass melt into a carbon mold. The glass ingots were machined into cylindrical parts having a diameter of 6 mm and a length of 4 mm which were glass materials to be measured for a rate of deformation and viscosity.

Primary heat treatment

Using an electric furnace, the glass materials were subject to primary heat treatment at 600° to 780° C. for 12 hours or less. Some glass materials were not subject to primary heat treatment.

Rate of deformation

The glass material was placed in an electric furnace and heated at a heating rate of 5° C./min. while longitudinally compressed under an initial pressure force of 1.8 MPa, and thereafter heated to 1,000° C. while maintaining a constant load. An alumina plate of 40 mm×40 mm was interposed between the pusher used for compression and the glass material to ensure a fully wide area. The rate of deformation was evaluated "⊙" when it was from 85% to less than 90% and "○" when it was 90% or more. The results are shown in the Tables.

Secondary heat treatment

The glass materials were subject to heat treatment under the conditions shown in the Tables. After the heat treatment, the materials were pulverized into powder and analyzed by powder X-ray diffraction (XD-D1 manufactured by Shimazu Mfg. K.K.). Several glass materials showed definite peaks indicative of the above-mentioned and other crystals and the remaining glass materials such as No. 307 in Table 3 did not show definite peaks.

Next, glass materials were prepared as above except that they had a diameter of 10 mm and a height of 4 mm. Each glass material after the secondary heat treatment was mirror finished on its opposed surfaces, obtaining a test sample having a diameter of 10 mm and a height of 2 mm. The sample was placed on a printed matter where lines of 2 mm wide were printed, for judging whether the lines were visually identifiable. As a result, all the glass materials shown in the Tables were semi-transparent or opaque. In these glass materials, a high crystallinity layer was not observed near the surface.

Acid and water resistance

The glass material after the secondary heat treatment was pulverized and classified, from which 3 grams of a fraction having a particle size of 420 to 590 μm was exactly weighed as a test powder. The test powder was boiled in 100 ml of a test solution (0.01N nitric acid solution or purified water) for one hour and dried before a percent weight loss was calculated. The results are shown in the Tables.

Flexural strength

The glass material after secondary heat treatment was polished on its surfaces with diamond paste to a mirror finish, obtaining a specimen of 3 mm×4 mm×35 mm. Flexural strength was measured by a three-point bend test using a strength tester ServoPulser EHF-F1 (manufactured by Shimazu Mfg. K.K.) at a crosshead speed of 0.5 mm/min. and a span of 15 mm. Except for shape, the specimen was prepared by the same procedure as the glass materials. The results are shown in the Tables.

TABLE 1

| Glass No. | 101 | 102 | 103 | 104 | 105 | 106 | 107 | 108 | 109 |
|---|---|---|---|---|---|---|---|---|---|
| Composition wt % | | | | | | | | | |
| SiO$_2$ | 59.7** | 48.3 | 61.7** | 54.6* | 46.3 | 56.3** | 48.1 | 46.5 | 54.3* |
| MgO | 23.0 | 27.2** | 19.5 | 18.4 | 17.2 | 19.5 | 21.2 | 14.7 | 23.5 |
| Al$_2$O$_3$ | 9.2* | 16.3 | 9.3* | 14.1 | 18.7 | 12.4 | 20.3 | 18.8 | 13.9 |
| TiO$_2$ | 8.1 | 8.2 | 6.4** | 6.6** | 6.1** | 9.0 | 6.8** | 8.3 | 8.3 |
| CaO | — | — | — | — | 3.1 | — | — | 8.7 | — |
| BaO | — | — | — | 4.5 | — | — | — | — | — |
| ZnO | — | — | — | — | 4.1 | — | — | — | — |
| Li$_2$O | — | — | 3.1 | — | — | — | — | — | — |
| Na$_2$O | — | — | — | — | 3.5 | — | — | — | — |
| K$_2$O | — | — | — | — | — | — | 2.3 | — | — |
| P$_2$O$_5$ | — | — | — | — | — | — | — | 3.0 | — |
| ZrO$_2$ | — | — | — | 1.8 | — | — | 1.3 | — | — |

TABLE 1-continued

| Glass No. | 101 | 102 | 103 | 104 | 105 | 106 | 107 | 108 | 109 |
|---|---|---|---|---|---|---|---|---|---|
| $B_2O_3$ | — | — | — | — | 1.0 | 2.8 | — | — | — |
| $\{100 - (A + S + T)\}/S$ | 0.385* | 0.563 | 0.366** | 0.452 | 0.624 | 0.396* | 0.516 | 0.568 | 0.433 |
| $(S + M)/4$ | 20.68 | 18.88 | 20.3 | 18.25 | 15.88 | 18.95 | 17.33 | 15.3 | 19.45 |
| Rate of deformation | ○ | ○ | ○ | ○ | ○ | ○ | ○ | ○ | ○ |
| Secondary heat treatment (°C.) | 910 | 880 | 900 | 890 | 950 | 900 | 890 | 890 | 890 |
| Treating time (hr) | 0.5 | 0.5 | 0.5 | 0.5 | 3 | 0.5 | 0.5 | 0.75 | 0.5 |
| Flexural strength (MPa) | 246 | 230 | 218 | 130 | 150 | 167 | 213 | 201 | 144 |
| Acid resistance (% weight loss) | 0.035 | 0.055 | 0.101 | 0.048 | 0.061 | 0.044 | 0.047 | 0.114 | 0.069 |
| Water resistance (% weight loss) | 0.003 | 0.002 | 0.054 | 0.004 | 0.015 | 0.009 | 0.008 | 0.011 | 0.005 |

***Outside the scope of the invention
**Outside the preferred range
*Outside the more preferred range

TABLE 2

| Glass No. | 201 | 202 | 203 | 204 | 205 |
|---|---|---|---|---|---|
| Composition wt % | | | | | |
| $SiO_2$ | 49.0 | 45.0 | 46.0 | 42.9 | 42.1 |
| MgO | 17.0 | 17.1 | 19.9 | 19.0 | 10.0* |
| $Al_2O_3$ | 25.9* | 29.8* | 26.0* | 30.0* | 30.0* |
| $TiO_2$ | 8.1 | 8.1 | 8.1 | 8.1 | 8.2 |
| CaO | — | — | — | — | 9.7 |
| $\{100 - (A + S + T)\}/S$ | 0.347** | 0.380* | 0.433 | 0.443 | 0.468 |
| $(S + M)/4$ | 16.5 | 15.53 | 16.48 | 15.48 | 13.03 |
| Rate of deformation | ○ | ○ | ◎ | ◎ | ◎ |
| Secondary heat treatment (°C.) | 880 | 910 | 910 | 910 | 890 |
| Treating time (hr) | 2 | 0.5 | 0.5 | 0.5 | 0.75 |
| Flexural strength (MPa) | 280 | 271 | 240 | 268 | 146 |
| Acid resistance (% weight loss) | 0.013 | 0.021 | 0.031 | 0.058 | 0.056 |
| Water resistance (% weight loss) | 0.009 | 0.003 | 0.012 | 0.014 | 0.009 |

***Outside the scope of the invention
**Outside the preferred range
*Outside the more preferred range

TABLE 3

| Glass No. | 301 | 302 | 303 | 304 | 305 | 306 | 307 | 308 | 309 |
|---|---|---|---|---|---|---|---|---|---|
| Composition wt % | | | | | | | | | |
| $SiO_2$ | 49.9 | 47.7 | 44.0 | 50.0 | 45.5 | 49.0 | 49.6 | 46.0 | 40.9 |
| MgO | 22.0 | 23.7 | 21.1 | 15.1 | 25.3 | 12.2 | 12.4 | 12.8 | 17.1 |
| $Al_2O_3$ | 20.0 | 20.3 | 10.7 | 11.0 | 11.5 | 15.5 | 13.6 | 16.2 | 15.2 |
| $TiO_2$ | 8.1 | 8.3 | 12.5 | 12.2 | 10.4 | 11.1 | 12.1 | 12.2 | 12.4 |
| CaO | — | — | 11.7 | 11.7 | 7.3 | 12.2 | 12.3 | 12.8 | 14.4 |
| MnO | — | — | — | — | — | — | — | — | — |
| $CeO_2$ | — | — | — | — | — | — | — | — | — |
| FeO | — | — | — | — | — | — | — | — | — |
| NiO | — | — | — | — | — | — | — | — | — |
| Ag | — | — | — | — | — | — | — | — | — |
| $\{100 - (A + S + T)\}/S$ | 0.441 | 0.497 | 0.746 | 0.536 | 0.716 | 0.498 | 0.498 | 0.557 | 0.77 |
| $(S + M)/4$ | 17.98 | 17.85 | 16.28 | 16.28 | 17.7 | 15.3 | 15.5 | 14.7 | 14.5 |
| Rate of deformation | ◎ | ◎ | ◎ | ◎ | ◎ | ◎ | ◎ | ◎ | ◎ |
| Secondary heat treatment (°C.) | 910 | 930 | 91 | 910 | 910 | 890 | 890 | 890 | 890 |
| Treating time (hr) | 0.5 | 1 | 0.75 | 0.75 | 0.75 | 0.75 | 0.75 | 0.75 | 0.5 |
| Flexural strength (MPa) | 232 | 257 | 152 | 290 | 220 | 230 | 276 | 211 | 199 |
| Acid resistance (% weight loss) | 0.027 | 0.023 | 0.066 | 0.059 | 0.031 | 0.032 | 0.049 | 0.035 | 0.022 |
| Water resistance (% weight loss) | 0.005 | 0.007 | 0.006 | 0.004 | 0.006 | 0.005 | 0.004 | 0.006 | 0.002 |

***Outside the scope of the invention
**Outside the preferred range
*Outside the more preferred range

TABLE 4

| Glass No. | 401 | 402 | 403 | 404 | 405 |
|---|---|---|---|---|---|
| Composition wt % | | | | | |
| $SiO_2$ | 48.9 | 49.7 | 48.8 | 49.9 | 49.9 |
| MgO | 14.7 | 14.9 | 12.0 | 12.0 | 15.3 |
| $Al_2O_3$ | 10.9 | 11.0 | 15.9 | 14.0 | 10.5 |
| $TiO_2$ | 11.7 | 11.9 | 10.9 | 12.0 | 12.0 |
| CaO | 11.7 | 11.8 | 11.9 | 11.9 | 12.0 |
| MnO | 0.2 | — | 0.2 | 0.1 | 0.1 |
| $CeO_2$ | 0.6 | — | 0.3 | — | — |
| FeO | 0.2 | — | — | 0.1 | — |
| NiO | 0.3 | — | — | — | 0.2 |
| Ag | 0.8 | 0.7 | — | — | — |
| {100 − (A + S + T)}/S | 0.583 | 0.551 | 0.5 | 0.483 | 0.553 |
| (S + M)/4 | 15.9 | 16.15 | 15.2 | 15.48 | 16.3 |
| Rate of deformation | ◎ | ◎ | ◎ | ○ | ◎ |
| Secondary heat treatment (°C.) | 900 | 900 | 890 | 890 | 900 |
| Treating time (hr) | 1 | 1 | 1 | 1 | 1 |
| Flexural strength (PMa) | 270 | 248 | 201 | 234 | 262 |
| Acid resistance (% weight loss) | 0.051 | 0.043 | 0.031 | 0.038 | 0.063 |
| Water resistance (% weight loss) | 0.006 | 0.005 | 0.004 | 0.007 | 0.005 |

***Outside the scope of the invention
**Outside the preferred range
*Outside the more preferred range As seen from the Tables, the glass materials of the invention have a high rate of deformation at temperatures of up to 1,000° C., satisfactory acid and water resistance, and sufficient flexural strength. Especially Nos. 203, 204 and 205 in Table 2, and glass materials in Tables 3 and 4 have a high rate of deformation. Nos. 201 and 202 in Table 2 have satisfactory acid resistance. Since the glass materials of the composition shown in Table 2 have a higher working temperature than the glass materials in Tables 3 and 4, bubbles are not effectively removed unless the temperature of glass melt is made higher or the melting time (time when glass remains molten) is prolonged. Then in preparing the glass materials of Table 2, the melting time was prolonged to fully remove bubbles. When a glass material of the same composition as shown in Table 2 was prepared with the melting time being the same as in the preparation of the glass materials of Tables 3 and 4, bubbles were left in the glass material.

Viscosity chancre of glass material

The glass materials shown in Table 5 were determined for a change of viscosity while they were heated to 1,000° C. at a heating rate of 5° C./min. For comparison purpose, glass materials whose composition was outside the scope of the invention were similarly measured. The results are shown in FIGS. 14 to 18.

Like the measurement of a rate of deformation, the viscosity change was measured on the glass material (in the form of a cylinder having a diameter of 6 mm and a length of 4 mm) after the primary heat treatment. For measurement, the method described in NEW GLASS, Vol. 4, No. 1, page 75 (1989) was used at a heating rate of 5° C./min.

TABLE 5

| Glass No. | 201 | 202 | 203 | 301 | 204 | 205 | 302 | 304 |
|---|---|---|---|---|---|---|---|---|
| Composition wt % | | | | | | | | |
| $SiO_2$ | 49.0 | 45.0 | 46.0 | 49.9 | 42.9 | 42.1 | 47.7 | 50.0 |
| MgO | 17.0 | 17.1 | 19.9 | 22.0 | 19.0 | 10.0* | 23.7 | 15.1 |
| $Al_2O_3$ | 25.9* | 29.8* | 26.0* | 20.0 | 30.0* | 30.0* | 20.3 | 11.0 |
| $TiO_2$ | 8.1 | 8.1 | 8.1 | 8.1 | 8.1 | 8.2 | 8.3 | 12.2 |
| CaO | — | — | — | — | — | 9.7 | — | 11.7 |
| $CaF_2$ | — | — | — | — | — | — | — | — |
| {100 − (A + S + T)}/S | 0.347** | 0.380* | 0.433 | 0.441 | 0.443 | 0.468 | 0.497 | 0.536 |

***Outside the scope of the invention
**Outside the preferred range
*Outside the more preferred range

TABLE 6

| Glass No. | 601 | 602 | 603 | 604 | 605 |
|---|---|---|---|---|---|
| Composition wt % | | | | | |
| $SiO_2$ | 57.4* | 51.8 | 48.0 | 49.8 | 46.0 |
| MgO | 13.9 | 13.7 | 13.7 | 13.7 | 13.7 |
| $Al_2O_3$ | 20.5 | 26.4* | 30.1* | 26.4* | 30.1* |
| $TiO_2$ | 8.2 | 8.1 | 8.2 | 8.1 | 8.2 |
| CaO | — | — | — | — | — |
| $CaF_2$ | — | — | — | 2.0* | 2.0* |
| {100 − (A + S + T)}/S | 0.242*** | 0.264*** | 0.285*** | 0.315*** | 0.341** |

***Outside the scope of the invention
**Outside the preferred range
*Outside the more preferred range Glass material Nos. 602 to 605 in Table 6 have compositions within the scope described in "Fine Ceramics," Vol. 3, pp. 79–87, 1982. Since these glass materials do not satisfy the above-mentioned expression I or satisfy the above-mentioned expression I, but contain fluorine, they experienced a rapid rise of viscosity midway heating as shown in FIGS. 14 to 18, as opposed to the glass materials of the invention. More particularly, the glass materials of the invention maintained the state that $\log\eta$ was up to 7.6 for at least 7 minutes whereas the glass materials of comparative examples could not maintain the state that $\log\eta$ was up to 7.6 for at least 7 minutes. The glass materials of comparative examples were also measured for a rate of deformation by the same procedure as above to find No. 602 66.5%, No. 603 80.5%, No. 604 78%, and No. 605 84%, which were lower than the rate of deformation of the glass materials of the invention.

Understandably, the glass materials shown in Table 5 were selected from Tables 2 and 3. Other glass materials of the invention were similarly examined for a viscosity change to find that they all maintained the state that $\log\eta$ was up to 7.6 for at least 7 minutes. For the glass materials shown in Tables 3 and 4 and Nos. 203, 204 and 205 in Table 2, the minimum of $\log\eta$ during the heating step to 1,000° C. was 6.73 or less.

Density chancre

Glass material Nos. 205, 304 and 307 were heated to 950° C. to examine a density change in the step of turning opaque through crystallization. The maximum change of density was +1.8% for No. 205, −1.0% for No. 304, and −3.2% for No. 307, all falling in the range of −5% to +3%.

Orthodontic part

A glass ingot was prepared by a re-melting method. The glass composition was the same as glass No. 304 in Table 3. This glass ingot was molded into an orthodontic part by applying a pressure of 0.15 MPa at 920° C. for 30 minutes. The molded body was substantially transparent. The shaped body was pulverized and examined for acid and water resistance by the same procedure as above. The acid resistance (% weight loss) was 0.060 and the water resistance (% weight loss) was 0.003. After the same heat treatment as molding was carried out on the glass ingot, flexural strength was measured as above to find 310 MPa.

The benefits of the invention are evident from the results of the foregoing Examples.

INDUSTRIAL APPLICABLE FIELD

The glass material of the invention can be pressure molded by utilizing the viscous flow phenomenon which occurs at temperatures in the range from the glass transition temperature to less than the liquidus temperature when the material is heated from a lower temperature side. Utilization of the viscous flow of glass permits the glass material to be easily molded into a desired shape such as a dental crown within a short time without using a special manufacturing equipment. In addition, the temperature required for molding is as low as 1,000° C. or lower and the pressure applied is as low as about 5 MPa or lower.

Also, the living tissue replacement obtained by processing the glass material to be substantially semi-transparent or opaque through crystallization or the like has aesthetic appearance and fully satisfactory acid and water resistance. When applied as dental crowns or the like, dissolution and performance loss such as strength loss little occur even in a rigorous environment as in the oral cavity. Since prior art crystallized glass for dental crowns has less environment resistance and insufficient aesthetic appearance as dental crowns, it must be subject to porcelain baking or staining on the surface when it is applied as dental crowns. Such a dental crown can be deteriorated because the glass base is exposed when the dental crown is secured to the diseased site and fine dimensional errors are drilled off. In contrast, the living tissue replacement of the invention little deteriorates in the oral cavity and is substantially free from the risk of deterioration even when the glass base is exposed by dimensional error correction or other causes.

Moreover, the living tissue replacement of the invention possesses at least equal mechanical strength to prior art biotic crystallized glass essentially requiring the addition of alkali metal elements and phosphorus. The prior art crystallized glass has noble metals added for the purposes of improving aesthetic appearance, improving strength and reducing the working time upon crystallization although the addition of noble metals results in difficultly reproducible benefits and adds to the cost. In contrast, the living tissue replacement of the invention has superior aesthetic appearance and strength without addition of noble metals and can be briefly treated to be semi-transparent or opaque through crystallization or the like.

Like the living tissue replacement mentioned above, the orthodontic part of the invention can be prepared by pressure molding utilizing the viscous flow phenomenon. Even a complex shape can be easily prepared. Since the part has superior environment resistance in the oral cavity, good slippage to metallic arch wires, and high mechanical strength, it is effective for correcting dental malalignment. Because of full transparency available, the part is acceptable from the aesthetic standpoint.

All these facts reveals the effectiveness of the invention.

We claim:

1. A glass material for use in the preparation of living tissue replacements and orthodontic parts, comprising silicon oxide, magnesium oxide, aluminum oxide, and titanium oxide as main components, the content of these components, when calculated as $SiO_2$, MgO, $Al_2O_3$, and $TiO_2$, respectively, and expressed by percent by weight, being $SiO_2$ 40 to 65% by weight, MgO 9 to 30% by weight, $Al_2O_3$ 8 to 31% by weight, and $TiO_2$ 6 to 15% by weight, the material satisfying expression I:

$$\{100-(A+S+T)\}/S \geq 0.340 \qquad \text{I:}$$

wherein A, S and T are contents in % by weight of $Al_2O_3$, $SiO_2$, and $TiO_2$, respectively, and Expression II:

$$(S+M)/4 > 100-(S+M+A+T) \qquad \text{II:}$$

wherein M is a content in % by weight of MgO, and being substantially free of fluorine.

2. The glass material of claim 1 further comprising at least one of Ca, Ba, and Zn as an auxiliary component, wherein the sum of CaO+BaO+ZnO is up to 20% by weight when Ca, Ba, and Zn are calculated as CaO, BaO, and ZnO, respectively.

3. The glass material of claim 1 further comprising at least one of Pd, Pt, Ag, Au, Re, Ru, Rh, and Ir as an auxiliary component in a total content of up to 1% by weight.

4. The glass material of claim 1 further comprising at least one of Mn, Fe, Ni, and Ce as an auxiliary component, wherein the sum of MnO+FeO+NiO+CeO$_2$ is up to 2% by weight when Mn, Fe, Ni, and Ce are calculated as MnO, FeO, NiO, and CeO$_2$, respectively.

5. The glass material of claim 1 further comprising at least one of Li, Na, K, and P as an auxiliary component, wherein the sum of Li$_2$O+Na$_2$O+K$_2$O+P$_2$O$_5$ is up to 5% by weight when Li, Na, K, and P are calculated as Li$_2$O, Na$_2$O, K$_2$O, and P$_2$O$_5$, respectively.

6. The glass material of claim 1 further comprising Zr as an auxiliary component, wherein the content of ZrO$_2$ is up to 5% by weight when Zr is calculated as ZrO$_2$.

7. The glass material of claim 1 further comprising B as an auxiliary component, wherein the content of B$_2$O$_3$ is up to 5% by weight when B is calculated as B$_2$O$_3$.

8. The glass material of claim 1 further comprising nitrogen, wherein the content of Si$_3$N$_4$ is up to 4% by weight when nitrogen is calculated as Si$_3$N$_4$.

9. The glass material of claim 1 wherein when compressed under an initial pressure of 1.8 Mpa and then heated from its glass transition temperature to 1,000° C. at a rate of 5° C./min. while being compressed under a constant load, the material is deformable at least 85% in the pressure applied direction.

10. The glass material of claim 1 wherein the material has a viscosity η (P) and the material maintains for at least 7 minutes the state that logη is up to 7.6 when heated at a heating rate of 5° C./min. at a temperature of from the glass transition temperature to 1,000° C.

11. The glass material of claim 1 wherein the material has a viscosity η (P) and the minimum of logη is up to 7.0 when heated at a temperature of from the glass transition temperature to 1,000° C.

12. A living tissue replacement prepared by shaping a glass material, said glass material comprising silicon oxide, magnesium oxide, aluminum oxide, and titanium oxide as main components, the content of these components, when calculated as SiO$_2$, MgO, Al$_2$O$_3$, and TiO$_2$, respectively, and expressed by percent by weight, being SiO$_2$ 40 to 65% by weight, MgO 9 to 30% by weight, Al$_2$O$_3$ 8 to 31% by weight, and TiO$_2$ 6 to 15% by weight, the material satisfying expressing I:

$$\{100-(A+S+T)\}/S \geq 0.340 \qquad \text{I:}$$

wherein A, S and T are contents in % by weight of Al$_2$O$_3$, SiO$_2$, and TiO$_2$, respectively, and Expression II:

$$(S+M)/4 > 100-(S+M+A+T) \qquad \text{II:}$$

wherein M is a content in % by weight of MgO, and being substantially free of fluorine, and treating said glass material to be substantially semi-transparent or opaque.

13. An orthodontic part prepared by shaping a glass material, said glass material comprising silicon oxide, magnesium oxide, aluminum oxide, and titanium oxide as main components, the content of these components, when calculated as SiO$_2$, MgO, Al$_2$O$_3$, and TiO$_2$, respectively, and expressed by percent by weight, being SiO$_2$ 40 to 65% by weight, MgO 9 to 30% by weight, Al$_2$O$_3$ 8 to 31% by weight, and TiO$_2$ 6 to 15% by weight, the material satisfying expressing I:

$$\{100-(A+S+T)\}/S \geq 0.340 \qquad \text{I:}$$

wherein A, S and T are contents in % by weight of Al$_2$O$_3$, SiO$_2$, and TiO$_2$, respectively, and Expression II:

$$(S+M)/4 > 100-(S+M+A+T) \qquad \text{II:}$$

wherein M is a content in % by weight of MgO, and being substantially free of fluorine.

* * * * *